(12) United States Patent
Fenster et al.

(10) Patent No.: US 11,426,198 B2
(45) Date of Patent: Aug. 30, 2022

(54) BIOPSY APPARATUS

(71) Applicant: Aaron Fenster, London (CA)

(72) Inventors: Aaron Fenster, London (CA); Jeffrey Scott Bax, Lucan (CA)

( * ) Notice: Subject to any disclaimer, the term of this patent is extended or adjusted under 35 U.S.C. 154(b) by 40 days.

(21) Appl. No.: 16/893,997

(22) Filed: Jun. 5, 2020

(65) Prior Publication Data

US 2021/0000499 A1 Jan. 7, 2021

Related U.S. Application Data

(60) Provisional application No. 62/870,727, filed on Jul. 4, 2019.

(51) Int. Cl.
| | |
|---|---|
| *A61B 17/34* | (2006.01) |
| *A61B 6/02* | (2006.01) |
| *A61B 6/03* | (2006.01) |
| *A61B 6/04* | (2006.01) |
| *A61B 8/08* | (2006.01) |

(Continued)

(52) U.S. Cl.
CPC .......... *A61B 17/3403* (2013.01); *A61B 6/025* (2013.01); *A61B 6/037* (2013.01); *A61B 6/0414* (2013.01); *A61B 6/0428* (2013.01); *A61B 6/0435* (2013.01); *A61B 6/4417* (2013.01); *A61B 6/502* (2013.01); *A61B 6/5205* (2013.01); *A61B 8/0841* (2013.01);
(Continued)

(58) Field of Classification Search
None
See application file for complete search history.

(56) References Cited

U.S. PATENT DOCUMENTS

| | | |
|---|---|---|
| 4,058,114 A | 11/1977 | Soldner |
| 5,660,185 A | 8/1997 | Shmulewitz et al. |

(Continued)

FOREIGN PATENT DOCUMENTS

| | | |
|---|---|---|
| CN | 202397562 U | 8/2012 |
| WO | 2019/068955 A1 | 4/2019 |

OTHER PUBLICATIONS

Boctor et al., "Virtual Remote Center of Motion control for needle placement robots" Computer Aided Surgery, 2004; 9(5): 175-183 (Year: 2004).*

(Continued)

*Primary Examiner* — Colin T. Sakamoto
(74) *Attorney, Agent, or Firm* — Brunet & Co. Ltd.; Robert Brunet; Hans Koenig

(57) ABSTRACT

An apparatus is provided for assisting breast biopsy. The apparatus includes a biopsy guide, a support system that effects three-dimensional movement of the biopsy guide and a system for registering coordinates of a remote center of motion (RCM) of the biopsy guide with a coordinate system on an image of a breast obtained from a parallel plate radiology imager. The biopsy guide has a mounting plate and a needle gun mount and ultrasound transducer mount on the mounting plate in a common plane. A biopsy needle of a needle gun mounted on the needle gun mount and an image plane of an ultrasound transducer mounted on the ultrasound transducer mount have longitudinal axes in or parallel to the common plane, which intersect at the RCM. The position of the RCM with respect to the biopsy guide is unchanged when the needle gun and/or ultrasound transducer moves on the biopsy guide.

10 Claims, 22 Drawing Sheets

(51) Int. Cl.
*A61B 6/00* (2006.01)
*A61B 8/00* (2006.01)

(52) U.S. Cl.
CPC .... *A61B 8/4218* (2013.01); *A61B 2017/3409* (2013.01); *A61B 2017/3413* (2013.01)

(56) References Cited

U.S. PATENT DOCUMENTS

| | | | | |
|---|---|---|---|---|
| 5,820,623 | A * | 10/1998 | Ng | A61B 34/70 606/1 |
| 6,425,865 | B1 * | 7/2002 | Salcudean | A61B 8/0875 600/111 |
| 7,021,173 | B2 * | 4/2006 | Stoianovici | B25J 9/06 74/490.03 |
| 8,853,635 | B2 | 10/2014 | O'Connor | |
| 9,114,252 | B2 | 8/2015 | Yu et al. | |
| 2008/0314181 | A1 * | 12/2008 | Schena | A61B 34/70 74/469 |
| 2009/0234369 | A1 * | 9/2009 | Bax | A61B 17/3403 606/130 |
| 2010/0240989 | A1 * | 9/2010 | Stoianovici | A61B 34/30 600/429 |
| 2011/0162805 | A1 * | 7/2011 | Cheng | B25J 9/104 156/578 |
| 2012/0245455 | A1 * | 9/2012 | Bauman | A61B 17/3403 600/424 |
| 2013/0261553 | A1 * | 10/2013 | Sheldon | A61M 25/0113 604/117 |
| 2014/0039314 | A1 * | 2/2014 | Stoianovici | A61B 8/0841 600/439 |
| 2015/0297177 | A1 * | 10/2015 | Boctor | A61B 34/30 600/437 |
| 2016/0067732 | A1 * | 3/2016 | Nakamura | B05B 13/0405 427/427.2 |
| 2017/0333003 | A1 * | 11/2017 | Son | A61B 17/3403 |
| 2018/0304093 | A1 * | 10/2018 | Son | A61B 8/4209 |
| 2019/0380795 | A1 * | 12/2019 | Tsao | A61B 90/50 |
| 2020/0038116 | A1 * | 2/2020 | Toporek | G06T 7/73 |
| 2020/0188041 | A1 * | 6/2020 | Toporek | A61B 8/0841 |

OTHER PUBLICATIONS

Hadavand et al., "A Parallel Remote Center of Motion Mechanism for Needle-Based Medical Interventions" 5th IEEE RAS & EMBS International Conference on Biomedical Robotics and Biomechatronics (BioRob) Aug. 12-15, 2014. São Paulo, Brazil (Year: 2014).*

* cited by examiner

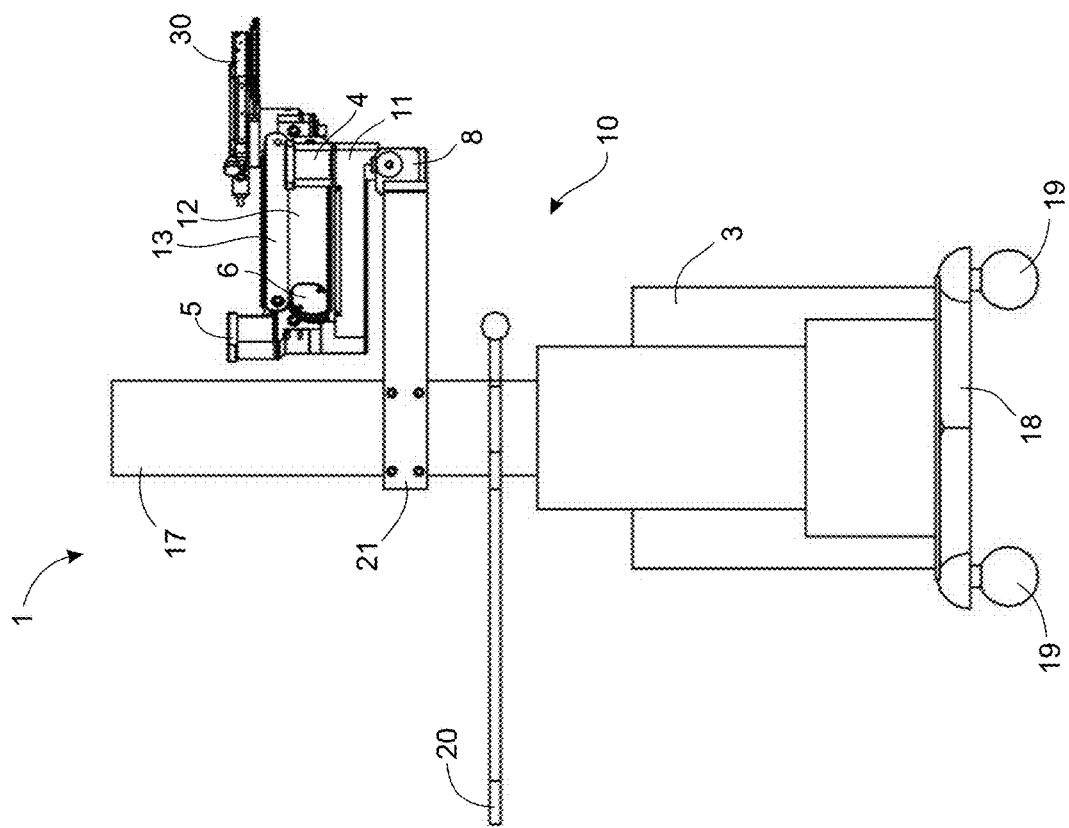
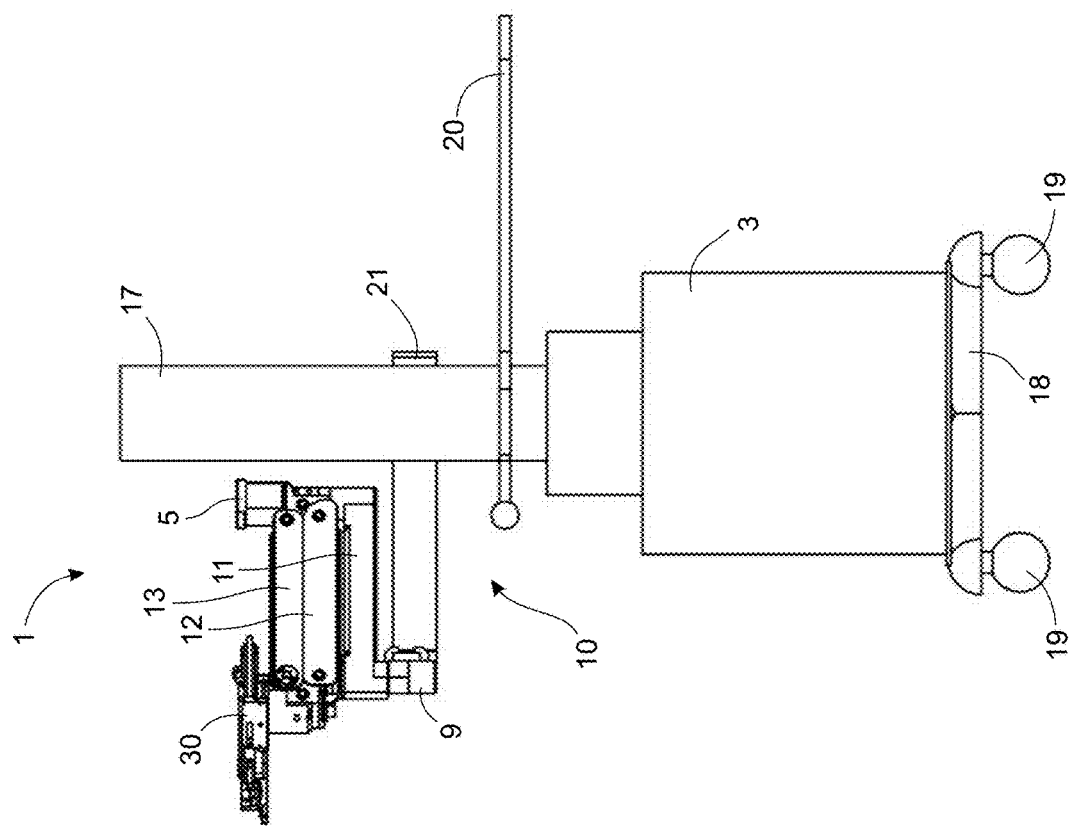

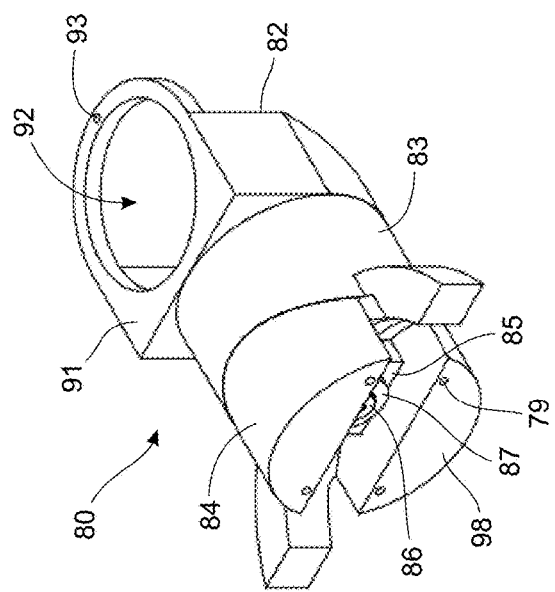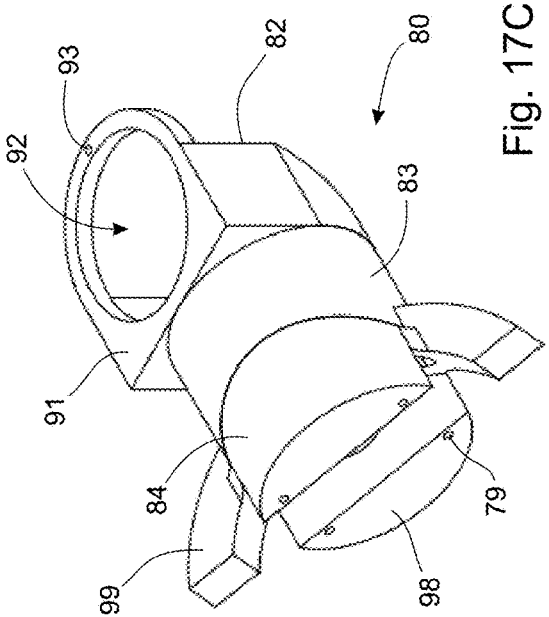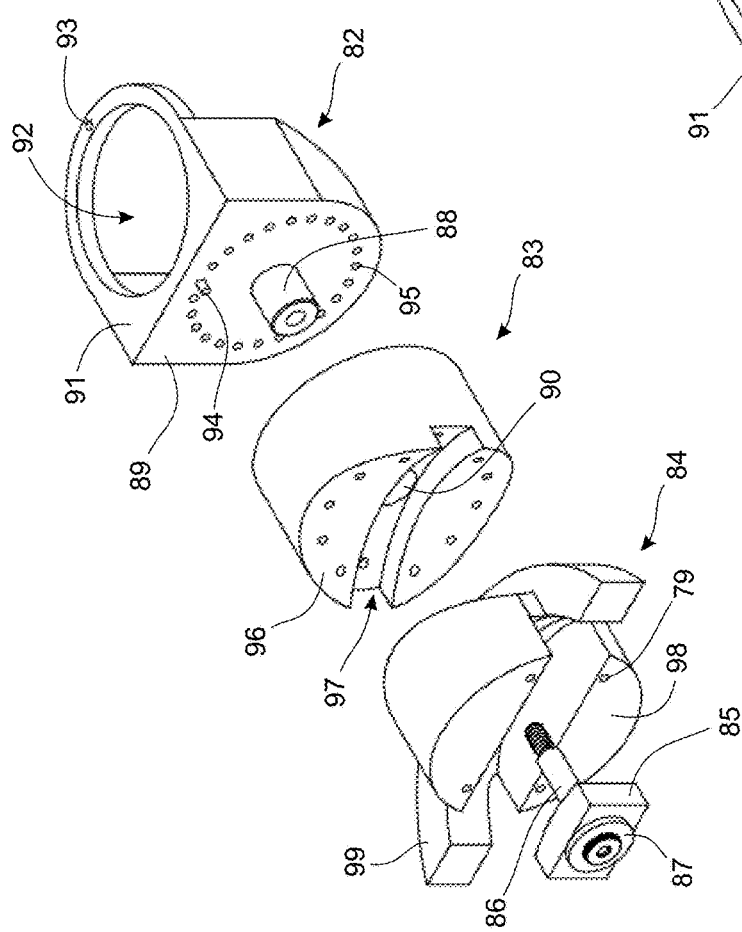
Fig. 17A
Fig. 17B
Fig. 17C ed States Pro-
BIOPSY APPARATUS

CROSS-REFERENCE TO RELATED APPLICATIONS

This application claims the benefit of United States Provisional patent application U.S. Ser. No. 62/870,727 filed Jul. 4, 2019, the entire contents of which is herein incorporated by reference.

FIELD

This application relates to biopsy apparatuses, especially to biopsy apparatuses for use with parallel plate radiology imaging such as positron emission mammography (PEM).

BACKGROUND

Parallel plate radiology imaging, for example X-ray mammography, stereo X-ray mammography, tomosynthesis and positron emission mammography (PEM), is used to locate a tumor in a breast of a subject. Parallel plate radiology imagers generally comprise a pair of plates placed above and below the breast. Mild breast compression may be applied to spread the breast and reduce thickness of the breast. In PEM, the pair of plates are both gamma radiation detectors. Radiation emitted by [$^{18}$F]-2-fluoro-2-deoxy-D-glucose (18F-FDG) injected into the breast and absorbed by a tumor annihilate on interaction with electrons in the tumor tissue, leading to the emission of a pair of photons travelling in opposite directions. The detection of two simultaneous photons by the detector plates indicates the emission of a positron at a point on the line linking the two detection events. An image is then reconstructed from the collected emission data. In X-ray mammography, stereo X-ray mammography, and tomosynthesis, one of the plates (usually an upper plate) is transparent to X-rays and in between the X-ray source (emitter), and the other plate (usually a lower plate) is an X-ray detector. Low energy X-rays emitted from the X-ray source pass through the breast where the X-rays interact differentially with different kinds of tissue. The X-rays after passing through the breast are detected by the lower plate, and an image is then reconstructed from the collected data.

While parallel plate radiology imaging is often used for discovery of a potential breast tumor, parallel plate radiology imagers can also be used to assist biopsy of the potential breast tumor. A biopsy involves removing a piece of the tumor using a needle or other surgical device. A parallel plate radiology imager may be used to locate the potential tumor in a breast while a surgical device is inserted in the breast to remove a piece of the tumor. However, because the two plates of the radiology imager limit the space for manipulating the surgical device, it is difficult to properly insert the surgical device along the correct path to the potential tumor. Any apparatus that assists with the insertion process must be slim enough to fit comfortably between the parallel plates, have sufficient degrees of freedom to correctly orient the surgical device along a line of penetration, be steady enough so that the line of penetration can be generally maintained and have a real-time monitoring capability to correct any misalignments of the surgical device during the penetration process.

There remains a need for an apparatus for assisting breast biopsy in association with parallel plate radiology imaging, which is simple to use without sacrificing requirement for performing a successful biopsy.

SUMMARY

In one aspect, there is provided an apparatus for assisting breast biopsy in association with parallel plate radiology imaging, the apparatus comprising: a biopsy guide comprising a mounting plate, a needle gun mount mounted on the mounting plate, and an ultrasound transducer mount mounted on the mounting plate, the ultrasound transducer mount mounted on the mounting plate in a common plane as the needle gun mount, wherein a biopsy needle of a needle gun when mounted on the needle gun mount and an image plane of an ultrasound transducer when mounted on the ultrasound transducer mount have longitudinal axes in or parallel to the common plane, the longitudinal axes intersecting at a center of motion (RCM) remote from the biopsy guide, wherein the needle gun when mounted on the needle gun mount and the ultrasound transducer when mounted on the ultrasound transducer mount are independently moveable parallel to the respective longitudinal axes of the biopsy needle and image plane, whereby a position of the RCM with respect to the biopsy guide is unchanged when the needle gun and/or ultrasound transducer is moved parallel to the respective longitudinal axes, and wherein the needle gun when mounted on the needle gun mount and the ultrasound transducer when mounted on the ultrasound transducer mount are independently arcuately moveable about the RCM along a common arcuate path, whereby the longitudinal axes move arcuately about the RCM when the needle gun and ultrasound transducer move along the common arcuate path, wherein a position of the RCM with respect to the biopsy guide is unchanged when the needle gun and/or the ultrasound transducer is moved along the common arcuate path on the mounting plate; a support system for supporting the biopsy guide, the support system comprising structures for effecting three-dimensional movement of the biopsy guide; and, a system for registering coordinates of the RCM with a coordinate system on an image of a breast of a subject obtained from a parallel plate radiology imager.

In another aspect, there is provided a method for performing a breast biopsy in association with parallel plate radiology imaging, the method comprising: obtaining an image of a breast using a parallel plate radiology imager, the image comprising a target spot identifying location of a target tumor in the breast; providing an apparatus comprising a biopsy guide and a support system for supporting the biopsy guide, the support system comprising structures for effecting three-dimensional movement of the biopsy guide, the biopsy guide comprising a needle gun mount and an ultrasound transducer mount mounted in a common plane as the needle gun mount, wherein a biopsy needle of a needle gun when mounted on the needle gun mount and an image plane of an ultrasound transducer when mounted on the ultrasound transducer mount have longitudinal axes in or parallel to the common plane, the longitudinal axes intersecting at a center of motion (RCM) remote from the biopsy guide; registering coordinates of the RCM with a coordinate system on the image; operating the structures for effecting three-dimensional movement of the biopsy guide to align the RCM with the target spot; operating the needle gun mounted on the biopsy guide to effect penetration of the biopsy needle into the breast followed by extraction of the biopsy needle from the breast; and, operating the ultrasound transducer to provide real-time ultrasound images of the biopsy needle as the biopsy needle penetrates the breast, samples the target tumor and is extracted from the breast.

The remote center of motion (RCM) of the biopsy guide remains unchanged with respect to the biopsy guide when the needle gun and/or the ultrasound transducer are moved on the biopsy guide. When the biopsy guide as a whole is moved by the structures of the support system, the RCM moves in space but does not move relative to the biopsy guide. Thus, the apparatus is simpler to use and construct requiring fewer position encoders to ensure that the biopsy needle is set in the correct position to perform the biopsy. Further, fewer calculations are required because there are fewer encoders, leading to faster operation of the apparatus.

Furthermore, the needle gun and ultrasound transducer are mounted in a common plane, thereby providing a slim profile permitting better physical access to the breast in the gap between the parallel plates of the radiology imager, while at the same time the needle gun and the ultrasound transducer can be adjusted on the biopsy guide to properly position the needle gun with respect to the subject and prevent the ultrasound transducer from interfering with the needle gun. Because the position of the RCM relative to the biopsy guide does not change when the needle gun and ultrasound transducer are adjusted on the biopsy guide, these adjustments can be made after the RCM is aligned with the position of the tumor in the breast without needing to re-align the RCM on the tumor position. Further, because needle gun and the ultrasound transducer are mounted in the common plane without the ability to move out of the common plane relative to each other, and the RCM always remains on the target spot once alignment of the RCM with the target spot is done, the target spot is always visible to the ultrasound transducer.

The parallel plate radiology imager (e.g. X-ray mammography imager, stereo X-ray mammography imager, tomosynthesis imager and positron emission mammography imager (PEM)) provides a static point for the biopsy needle to hit during the biopsy. Registering the RCM with that static point can be done prior to commencing the biopsy and does not change during the procedure ensuring great accuracy without the need for a highly skilled physician to operate the biopsy needle. At the same time, the ultrasound transducer can constantly provide real-time ultrasound images of the breast environment in which the biopsy needle is moving without interfering with the biopsy needle, the constant real-time images helping to confirm guidance of the biopsy needle and permitting corrections to be made to the movement of the biopsy needle, if required. While ultrasound imaging provides confirmation and the opportunity to make corrections, guidance of the biopsy needle is based on the image obtained from the parallel plate radiology imager.

Further features will be described or will become apparent in the course of the following detailed description. It should be understood that each feature described herein may be utilized in any combination with any one or more of the other described features, and that each feature does not necessarily rely on the presence of another feature except where evident to one of skill in the art.

BRIEF DESCRIPTION OF THE DRAWINGS

For clearer understanding, preferred embodiments will now be described in detail by way of example, with reference to the accompanying drawings, in which:

FIG. 4 depicts a left side view of the apparatus of FIG. 1;

FIG. 5 depicts a right side view of the apparatus of FIG. 1;

FIG. 17A depicts an exploded view of an adjustable adapter assembly that permits adapting the apparatus for assisting breast biopsy for mediolateral breast imaging and biopsy;

FIG. 17B depicts a perspective view of the adjustable adapter assembly of FIG. 17A in a first fixed configuration;

FIG. 17C depicts the adjustable adapter assembly of FIG. 17B in a second fixed configuration;

DETAILED DESCRIPTION

Figure 1:
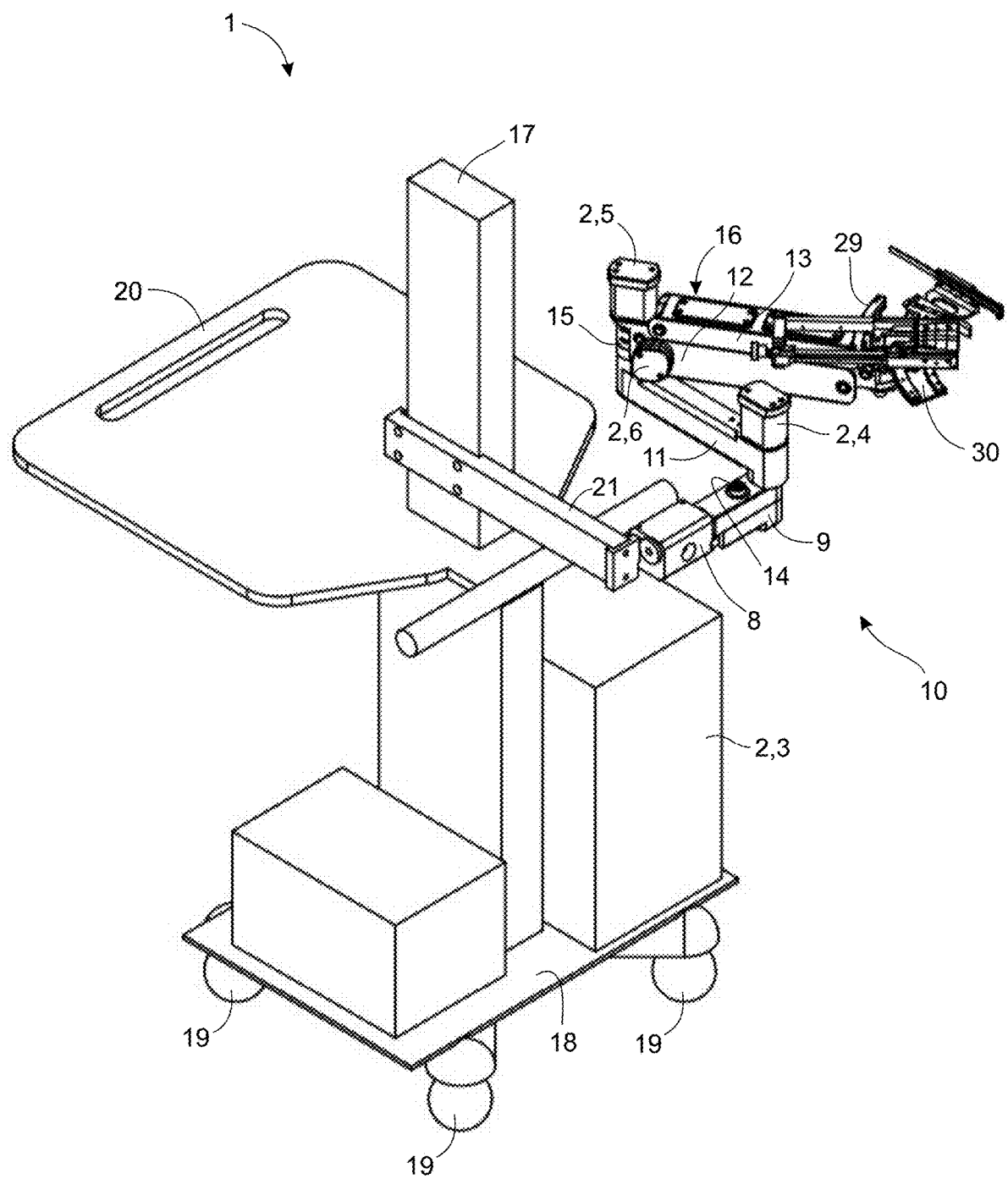
FIG. 1 depicts a perspective view of one embodiment of an apparatus for assisting breast biopsy.
Figure 3:
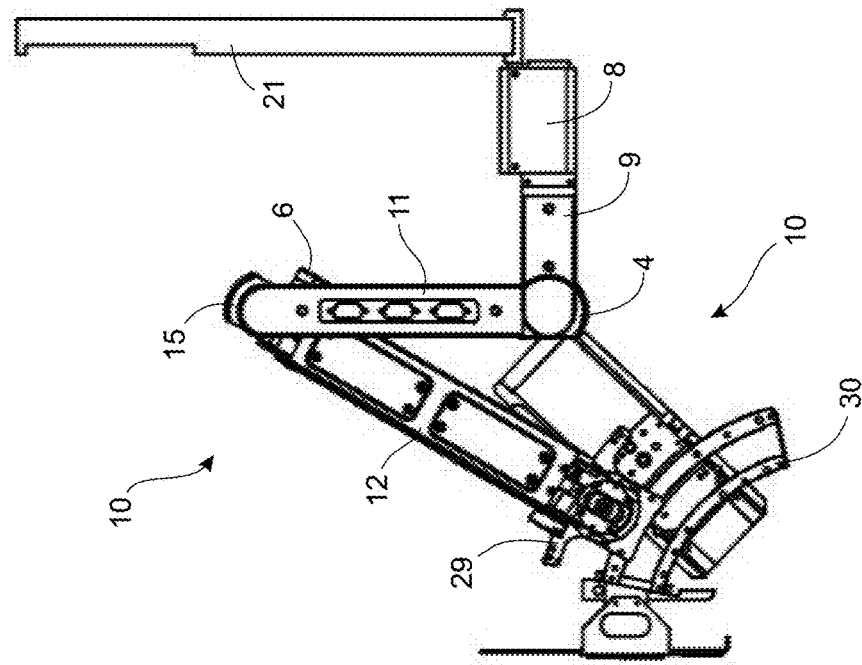
FIG. 3 depicts a bottom view of the apparatus of FIG. 1 without an operator work surface.
Figure 2:
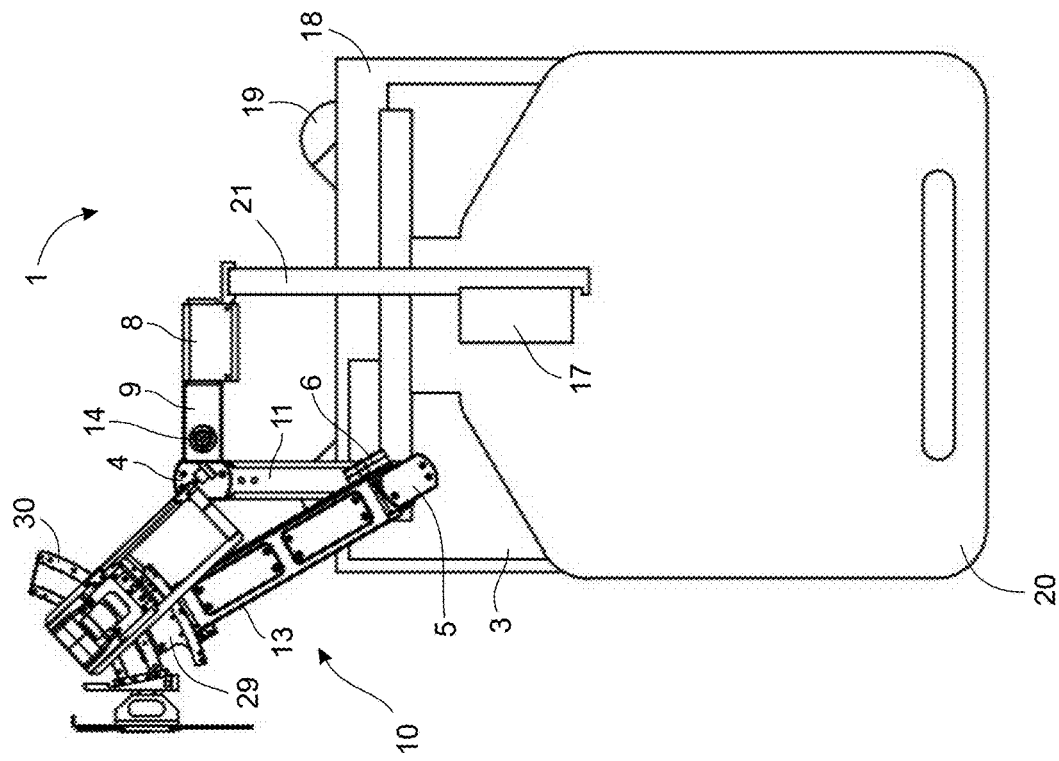
FIG. 2 depicts a top view of the apparatus of FIG. 1.
Figure 7:
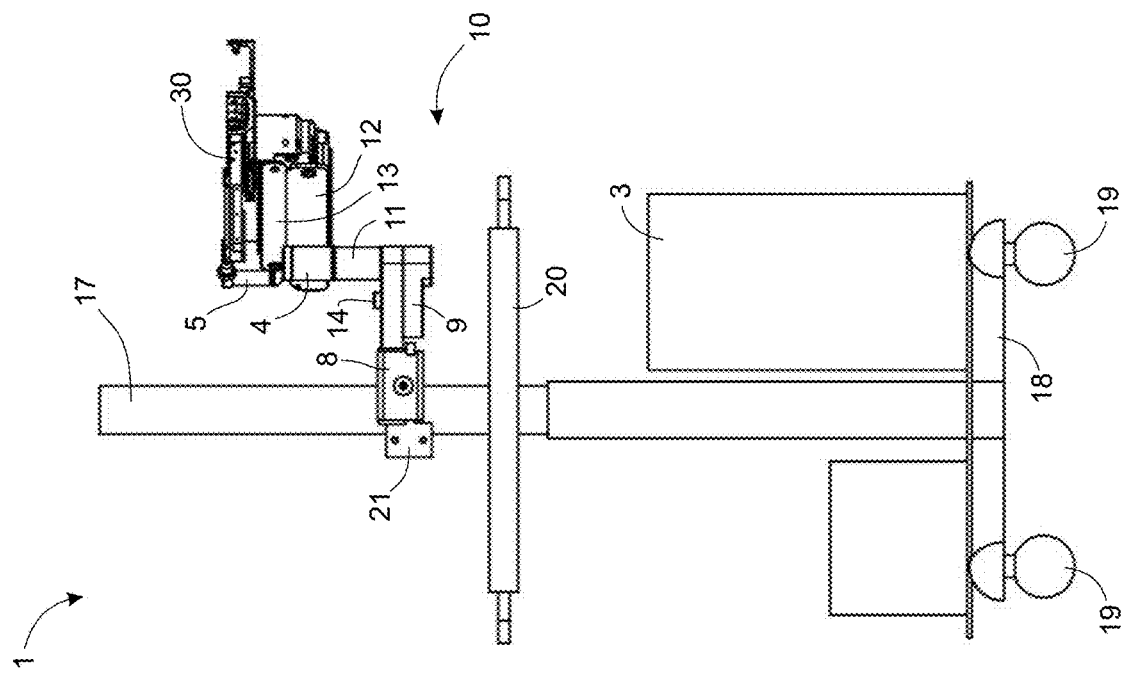
FIG. 7 depicts a rear end view of the apparatus of FIG. 1.
Figure 6:
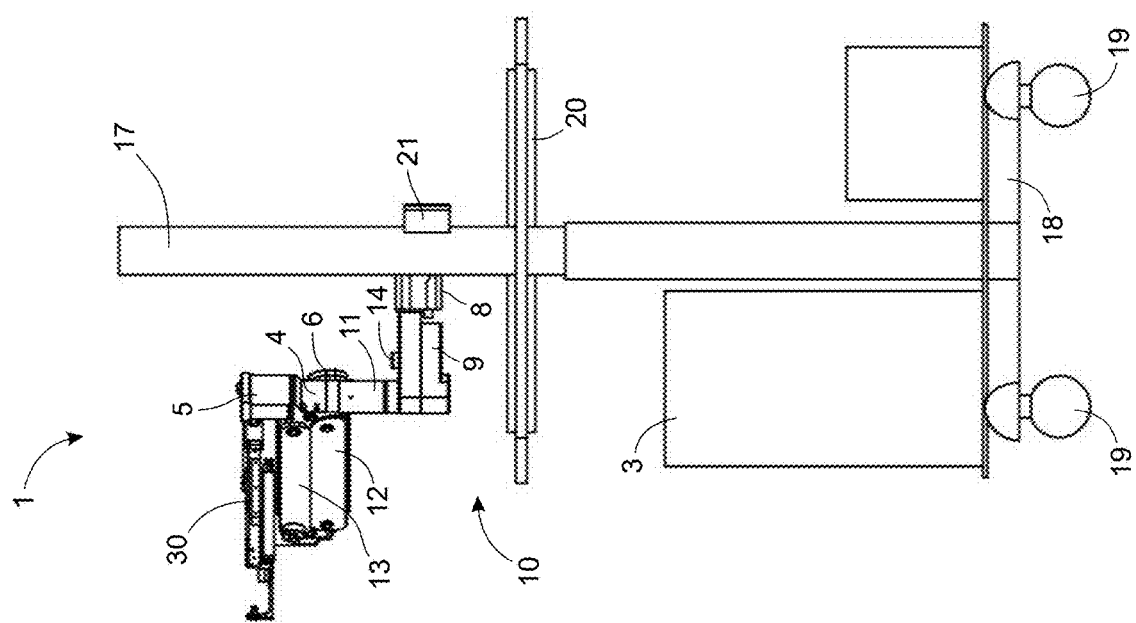
FIG. 6 depicts a front end view of the apparatus of FIG. 1.

With reference to the Figures generally, and in particular to FIG. 1 to FIG. 8A, in one embodiment, an apparatus 1 for assisting breast biopsy comprises a biopsy guide 30 mounted on a support system 10 for supporting the biopsy guide 30. The support system 10 comprises a first support arm 9, a second support arm 11, a third support arm 12 and a fourth support arm 13 pivotally linked in together. The third arm 12 and the fourth arm 13 are connected in parallel to form a parallelogram 16. The first arm 9, second arm 11 and the parallelogram 16 are linked in series. The third and fourth arms 12, 13 form adjacent sides of the parallelogram 16, the second support arm 11 is connected to a base 15 of the parallelogram 16. A mount structure 29 for the biopsy guide 30 forms a distal end of the parallelogram 16. The parallelogram 16 keeps the orientation of the biopsy guide 30 parallel to detector plates of a parallel plate imaging machine throughout the full range of motion of the biopsy guide 30.

The first arm 9 is mounted on a pivoting connection 8, the first arm 9 pivotable on the pivoting connection 8 about a first axis of rotation, which is an axis parallel with respect to the ground. The pivoting connection 8 can be loosened and tightened to permit or prevent rotation of the first arm 9 about the first axis of rotation. The second arm 11 is pivotally mounted to the first arm 9 so that the second arm 11 is pivotable about a second axis of rotation perpendicular to the first axis of rotation. The parallelogram 16 comprising the third arm 12 and fourth arm 13 is pivotally mounted to the parallelogram base 15, which in turn is pivotally mounted to the second arm 11 so that the parallelogram 16 is pivotable about a third axis of rotation parallel to but spaced apart from the second axis of rotation. The third and fourth arms 12, 13 are pivotally mounted to the base 15 of the parallelogram 16, the third and fourth arms 12, 13 pivotable about a fourth axis of rotation perpendicular to the second and third axes of rotation.

The biopsy guide 30 is rigidly mounted on the mount structure 29 at the distal end of the parallelogram at a position remote from the third axis of rotation. Pivoting of the second, third and fourth arms 11, 12, 13 about the axes of rotation controls the position of the biopsy guide 30 in space in three dimensions, where x, y adjustment is made with the second arm 11 and the parallelogram base 15 and z adjustment is made from relative movement of the fourth arm 13 to the third arm 12 in the parallelogram 16. Rotation of the first arm 9 about the first axis of rotation controls orientation of the biopsy guide 30 in space and is used to level the biopsy guide 30 perpendicular to gravity to prevent the second, third and fourth arms 11, 12, 13 form drifting when unlocked. A bull's eye level 14 on the first arm 9 is used to determine whether the biopsy guide 30 is leveled. The pivoting connection 8 is rigidly mounted on a mounting bar 21, the mounting bar 21 rigidly connected to a stand 17 supported on a cart 18 having casters 19 so that the apparatus 1 can be easily transported between locations. Instead of being supported on a cart, the support system could comprise a parallel plate imaging machine itself with the stand supported on the imaging machine. An operator work surface 20 mounted to the stand 17 provides a horizontal surface on which a control device may be supported so that an operator may control the apparatus 1, or on which the operator can perform other work.

Figures 8A, 8B:
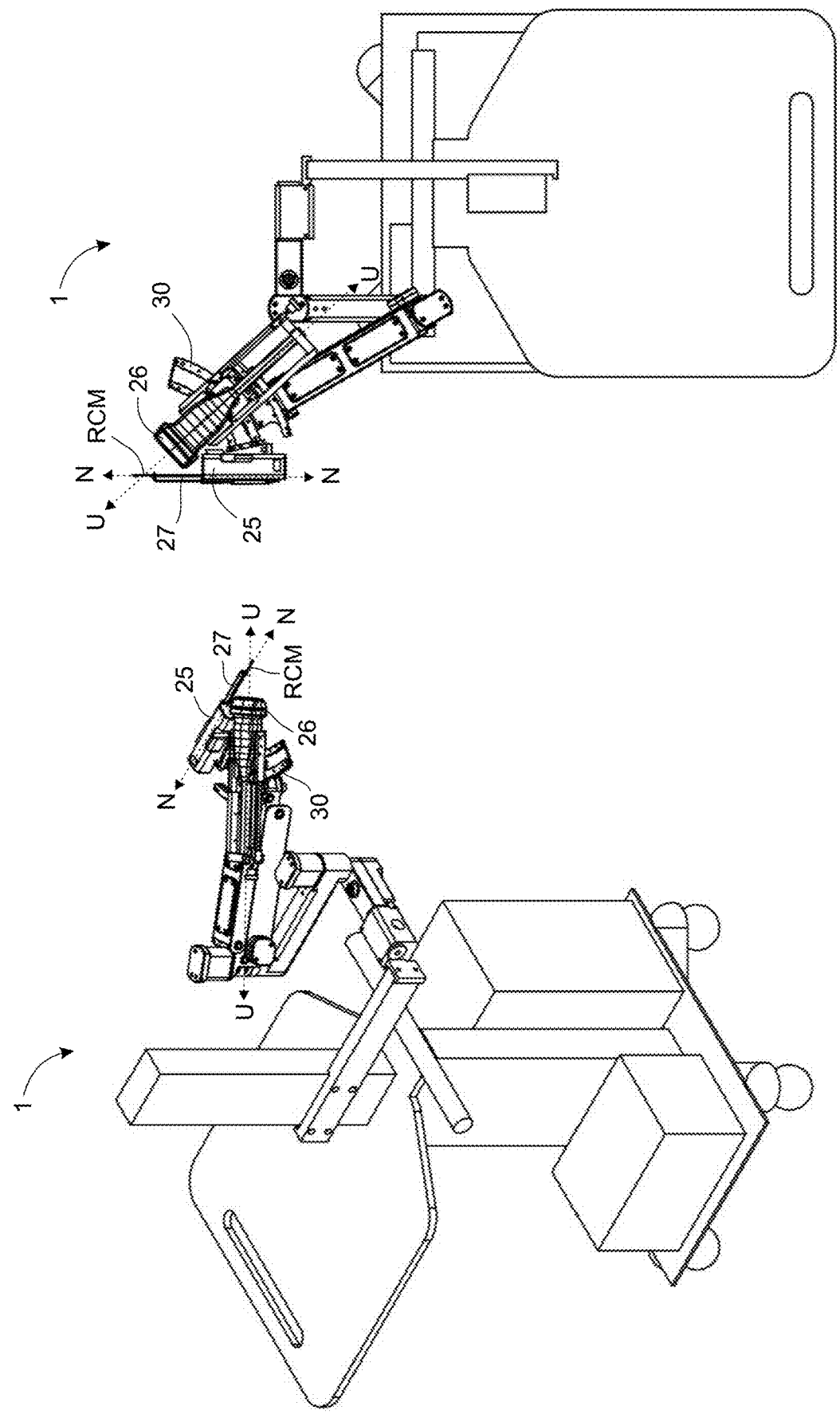
FIG. 8A depicts a perspective view of the apparatus of FIG. 1 having a needle gun and an ultrasound transducer mounted thereon.
FIG. 8B depicts a top view of the apparatus of FIG. 1 having a needle gun and an ultrasound transducer mounted thereon.
Figure 11A:
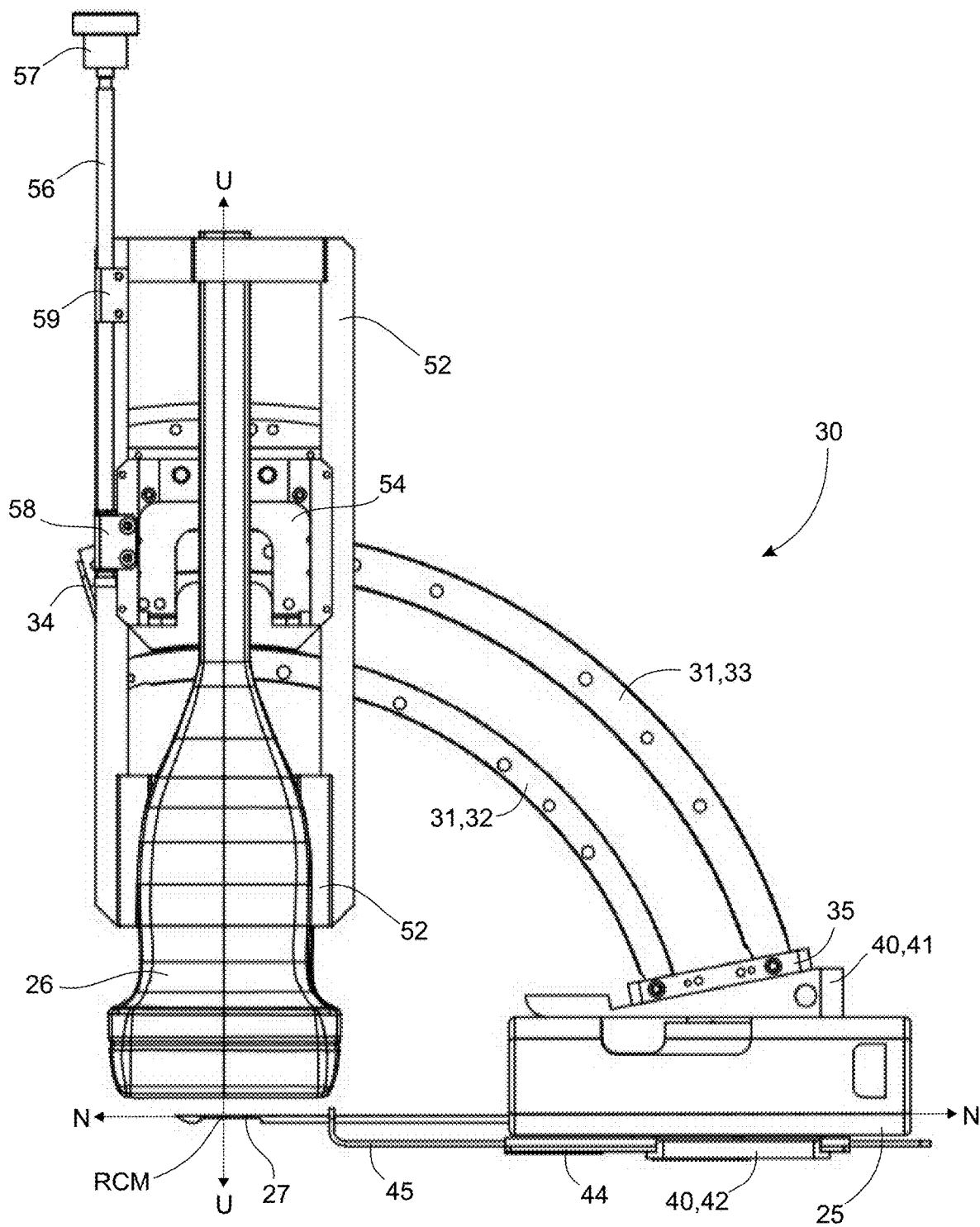
FIG. 11A depicts a top view of a biopsy guide of the apparatus of FIG. 1 having a needle gun and an ultrasound transducer mounted thereon in most arcuately separated positions from each other.
Figure 11B:
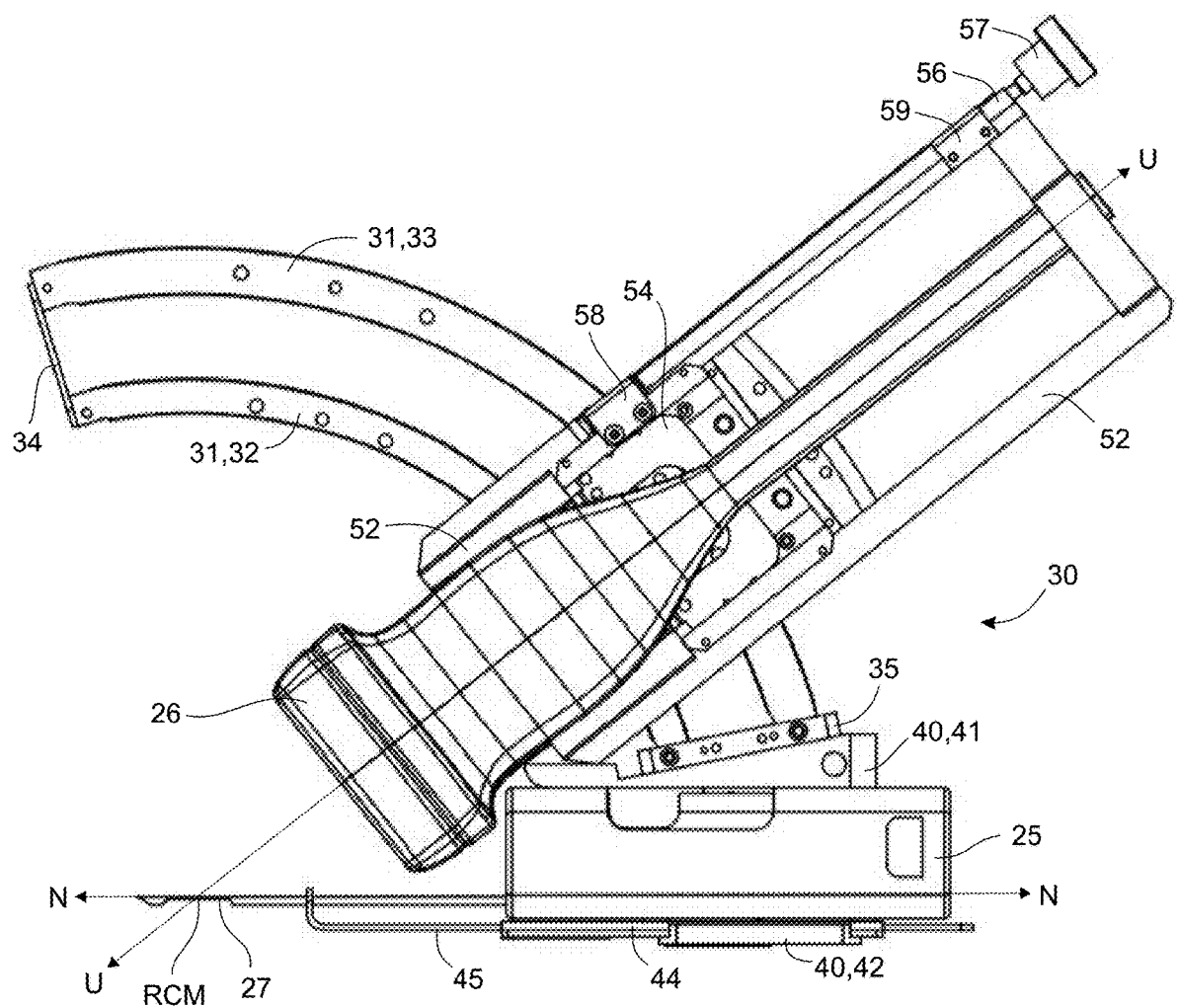
FIG. 11B depicts a top view of a biopsy guide of the apparatus of FIG. 1 having a needle gun and an ultrasound transducer mounted thereon in least arcuately separated positions from each other.
Figure 11C:
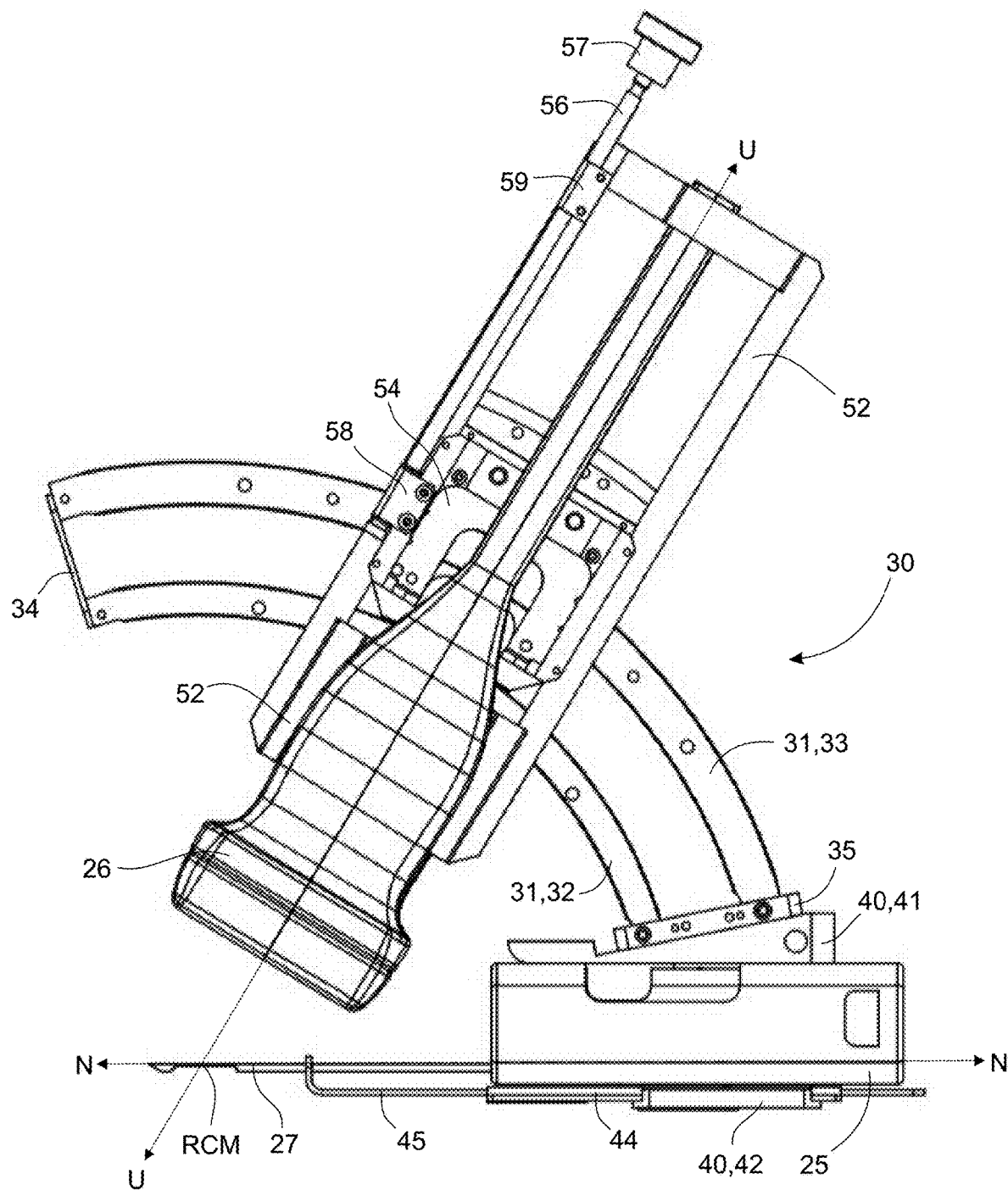
FIG. 11C depicts a top view of a biopsy guide of the apparatus of FIG. 1 having a needle gun and an ultrasound transducer mounted thereon in intermediate arcuately separated positions from each other.

As seen in FIG. 8A and FIG. 8B, when a needle gun 25 and an ultrasound transducer 26 are mounted on the biopsy guide 30, the needle gun 25 and ultrasound transducer 26 are mounted in a common plane with a longitudinal axis N-N of the needle gun 25, which defines a path along which a biopsy needle 27 follows during the breast biopsy, intersecting a longitudinal centerline U-U of an image plane of the ultrasound transducer 26 at a remote center of motion RCM about which the longitudinal axis N-N and the longitudinal centerline U-U rotate when the needle gun 25 and/or the ultrasound transducer 26 are arcuately moved on the biopsy guide 30 in the common plane, as further described in connection with FIG. 11A, FIG. 11B and FIG. 11C. The RCM is a point in space that is not on the biopsy guide 30.

The apparatus 1 further comprises a system 2 for registering coordinates of the RCM with a coordinate system on an image of a breast 101 of a subject 100. The system 2 comprises a computer 3 in electronic communication with first, second and third position encoders 4, 5, 6. The first position encoder 4 is mounted on the second arm 11 at the juncture to the first arm 9 to provide information about the angular position of the second arm 11 relative to the first arm 9. The second position encoder 5 is mounted on the parallelogram base 15 at the juncture to the second arm 11 to provide information about the angular position of the third arm 12, and therefore the parallelogram, relative to the second arm 11. The third position encoder 6 is mounted on the third arm 12 at one of the junctures to the parallelogram base 15 to provide information about the position of the fourth arm 13 relative to the third arm 12. The position encoders 4, 5, 6 provide information to the computer 3 about the position of the biopsy guide 30 in space. Because the RCM of the needle gun 25 and ultrasound transducer 26 of the biopsy guide 30 is invariant with respect to the positions of the needle gun 25 and ultrasound transducer 26 on the biopsy guide 30, the position encoders 4, 5, 6 are sufficient to provide to the computer 3 the position of the RCM in space. There is no need for additional position encoders to track position of the needle gun 25 and ultrasound transducer 26 in order to determine the position of the RCM in space. Nevertheless, additional position encoders may be employed, if desired.

The computer 3 is programmed with computer executable instructions for comparing the location of the RCM in space to position-related image data collected from imaging the breast 101 of the subject 100. The computer executable instructions also include instructions for controlling operation of the apparatus 1, including instructions for operating the arms 9, 11, 12, 13 based on visual information and information from the position encoders 4, 5, 6. While the support arms in the illustrated system are not motorized, an alternative embodiment may further comprise motors to drive pivoting/rotation of one or more of the arms. The motors may be positioned in series with the position encoders, and in electronic communication with the computer. The computer may be additionally programmed with computer executable instructions for operating the support arms. The operator work surface 20 and/or stand 17 may support one or more computer interfaces, for example input devices (e.g. keyboard, microphone, computer mouse, or the like) and/or output devices (e.g. monitor, speaker, printer or the like) that permit the operator to interact with the computer 3.

Figure 9B:
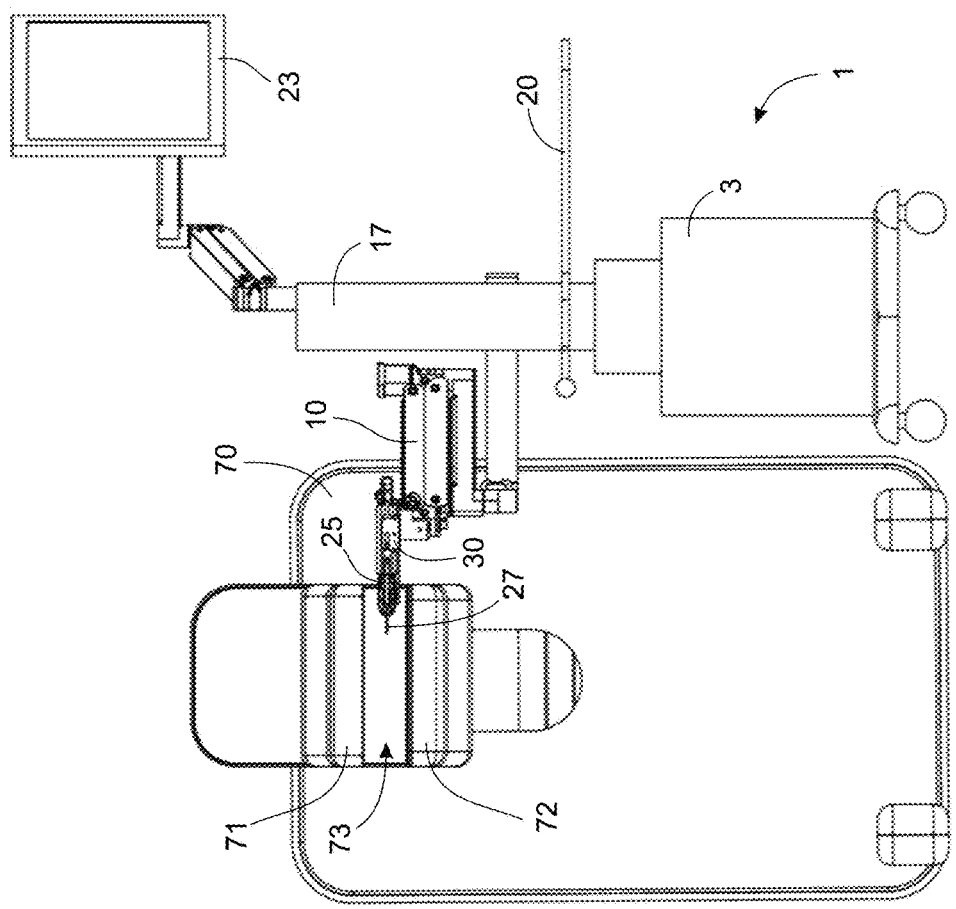
FIG. 9B depicts a side view of FIG. 9A.
Figure 9A:
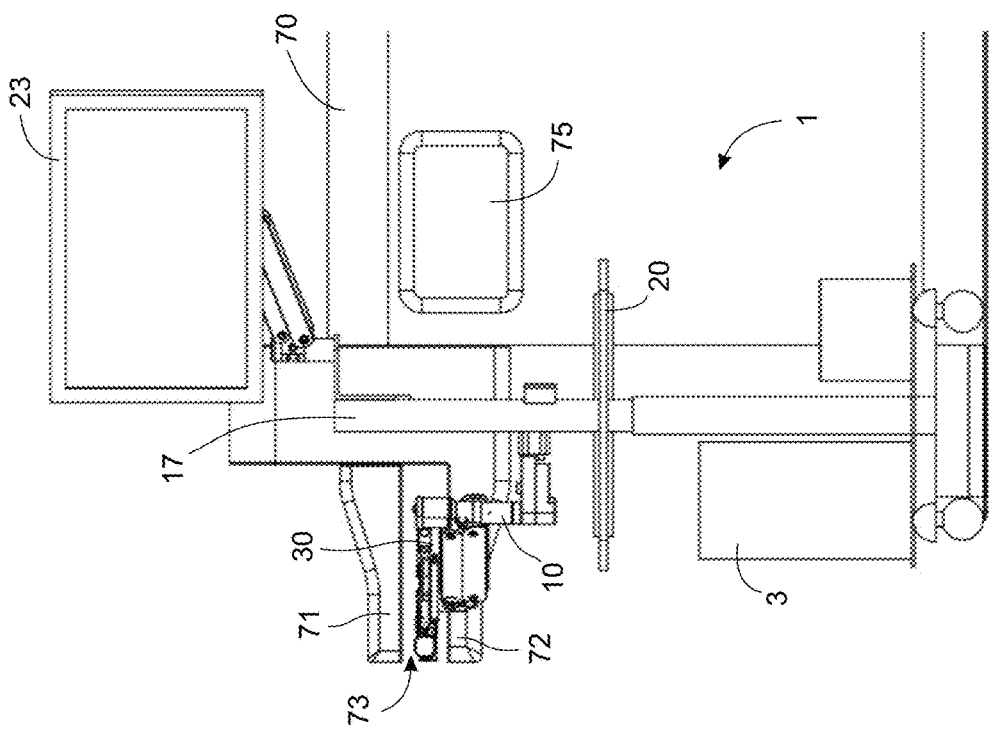
FIG. 9A depicts a front end view of the apparatus of FIG. 1 having a needle gun and an ultrasound transducer mounted thereon, in association with a parallel plate radiology imager.
Figure 10:
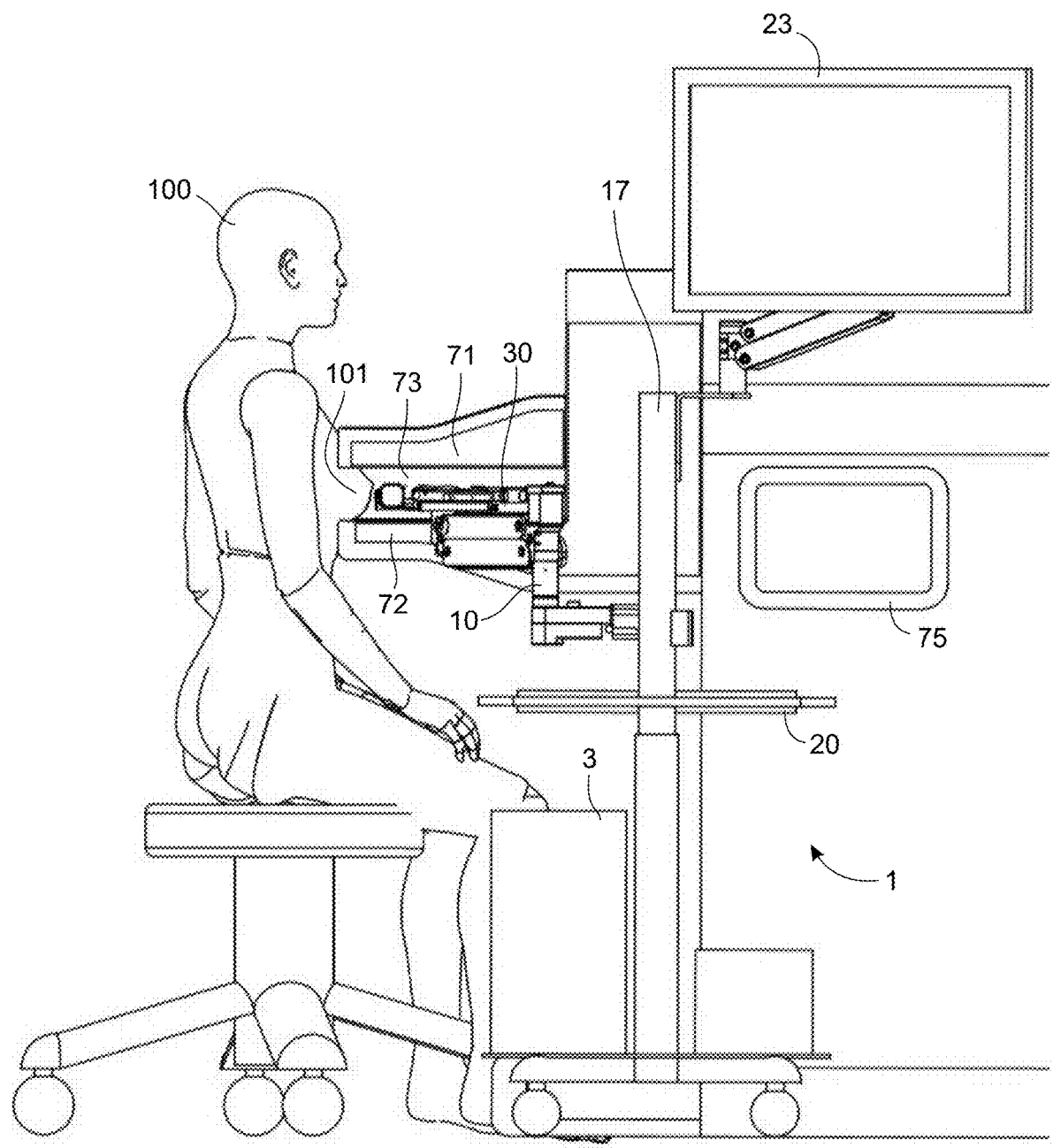
FIG. 10 depicts a front end view of the apparatus of FIG. 1 having a needle gun and an ultrasound transducer mounted thereon, in association with a parallel plate radiology imager with a subject in position for undergo a breast biopsy.

With particular reference to FIG. 9A, FIG. 9B and FIG. 10, the apparatus 1 for assisting breast biopsy is shown in association with a parallel plate radiology imager 70, for example a positron emission mammography (PEM) machine. The parallel plate radiology imager 70 comprises an upper plate 71 and a lower plate 72 vertically separated by a horizontal gap 73 within which the breast 101 of the subject 100 is placed. In the case of a PEM machine, the upper plate and the lower plate are both gamma detectors that detect the emission of gamma radiation from a radioactive compound injected into the breast 101, which accumulates in a tumor. In X-ray mammography, stereo X-ray mammography, and tomosynthesis, the upper plate is in between the emitter and bottom plate while the bottom plate is an X-ray detector. The apparatus 1 is positioned proximate the imager 70 so that the biopsy guide 30 may be readily manipulated by the arms 9 and 11 and the parallelogram (comprising the arms 12, 13) of the support system 10 to align the biopsy needle 27 substantially parallel to a chest wall of the subject 100, and to align the RCM with a target tumor T in the breast 101. The computer 3 of the apparatus 1 is electronically connected to a computer of the imager 70 and programmed to interface with the computer of the imager 70 so that coordinates of the RCM (i.e. the position in space of the RCM) can be registered with a coordinate system on an image of the breast 101 constructed from data collected by the parallel plates 71, 72. An operator can view the image and track the position of the RCM on a monitor 23 mounted on the stand 17 of the support system 10, or on a different monitor or other output device in a different location. Various functions of the imager 70 can be controlled from a control panel 75.

As can be seen in FIG. 9A, FIG. 9B and FIG. 10, the biopsy guide 30 with the needle gun 25 and ultrasound transducer 26 mounted thereon in the common plane has a slim enough profile so that when the common plane is sufficiently close to being coplanar with the parallel plates 71, 72, enough of the biopsy guide 30 can fit in the gap 73 between upper and lower plates 71, 72, thereby providing sufficient access to the breast 101 for both the biopsy needle 25 and ultrasound transducer 26 simultaneously. Thus, not only does the apparatus 1 provide a stable, steady position from which the biopsy needle 25 can access the target tumor T in the breast 101, the apparatus 1 also provides movement with sufficient degrees of freedom to correctly and accurately orient the biopsy needle 25 along a line of penetration determined by the parallel plate radiology imager 70, and provides real-time ultrasound monitoring capability to correct any misalignments of the biopsy needle 25 during the penetration process.

With particular reference to FIG. 11A, FIG. 11B and FIG. 11C, the biopsy guide 30 comprises a relatively thin mounting plate 31 mountable to the parallelogram of the support system 10, for example with tracks, bolts, clamps or the like through the mount structure 29 (see FIG. 12A) on the parallelogram. The mounting plate 31 comprises an inner arcuate track 32 and an outer arcuate track 33, the outer arcuate track 33 parallel to the inner arcuate track 32. The arcuate tracks 32, 33 are connected rigidly together at opposed ends by end plates 34, 35. The mounting plate 31 is therefore both flat (i.e. having a small height relative to a width and length of the mounting plate 31) and arcuate. The biopsy guide 30 further comprises a needle gun mount 40 and an ultrasound transducer mount 50, both of which have slim profiles and are mounted spaced-apart on the mounting plate 31 so that the mounts 40, 50 are in a common plane.

The needle gun mount 40 comprises a needle gun mount base 41, which is rigidly mounted to the mounting plate 31. The needle gun mount 40 further comprises a needle gun cradle 42 rigidly mounted on the needle gun mount base 41. While the needle gun mount base 41 is not moveable along the arcuate tracks 32, 33, in an alternative embodiment the needle gun mount base may be arcuately moveable along the arcuate tracks and lockable at any desired place on the mounting plate, for example with set screws. In the present embodiment, the mount structure 29 comprises a female arcuate track mated with the arcuate track 33 of the mounting plate 31, so that the mounting plate 31 can move arcuately on the mount structure 29. Set screws 36 are used to lock the mounting plate 31 in place on the mount structure 29. The needle gun cradle 42 is configured to accept the needle gun 25 therein such that the needle gun 25 is prevented from moving laterally but is moveable longitudinally along the longitudinal axis N-N of the needle gun 25. The needle gun cradle 42 comprises a needle gun stop 44, which is adjustable longitudinally with respect to the longitudinal axis N-N, and which may be lockable to prevent the needle gun 25 from moving in at least one, preferably both, longitudinal directions with respect to the longitudinal axis N-N. The needle gun cradle 42 further comprises an extendible needle support 45, which is adjustable longitudinally with respect to the longitudinal axis N-N, and which may be lockable or stoppable to prevent longitudinal movement of the needle support 45 in at least one, preferably both, longitudinal directions with respect to the longitudinal axis N-N. With the biopsy needle 27 loaded in the needle gun 25, the needle support 45 helps prevent or at least reduce lateral deflection of the biopsy needle 27 as the biopsy needle 27 penetrates the breast 101. The facility to move the needle gun 25 on the needle gun cradle 42 permits a surgeon or surgical robot to perform the breast biopsy by pushing the needle gun 25 toward the breast 101 on a stable and properly aligned platform until the biopsy needle 27 penetrates the breast 101 and reaches the target tumor T, and then retracting the needle gun 25 to remove the biopsy needle 27 from the breast 101. Setting and locking the needle gun stop 44 at an appropriate position derived from the position of the RCM prevents the biopsy needle 27 from being pushed too far.

The ultrasound transducer mount 50 comprises a transducer mount base 54 movably mounted on the arcuate tracks 32, 33 and a transducer cradle 52 movably mounted on the transducer mount base 54. The transducer mount base 54 comprises a pair of arcuate grooves on an underside thereof, which are mated with the arcuate tracks 32, 33 so that the transducer mount 50 is supported on the mounting plate 31 and the transducer mount base 54 can move arcuately along the arcuate tracks 32, 33. While no locking mechanism is provided, an alternative embodiment may provide a locking mechanism, for example set screws or bolts, to secure the transducer mount base immovably on the arcuate tracks. In an alternate embodiment, the mount structure may be made large enough so that the transducer mount base is also supported and moveable arcuately on the mount structure. The transducer cradle 52 is configured to accept the ultrasound transducer 26 therein such that the ultrasound transducer 26 is prevented from moving laterally and longitudinally in the transducer cradle 52. The transducer cradle 52 is movably mounted on the transducer mount base 54 so that the transducer cradle 52 can move longitudinally on the transducer mount base 54 along the centerline U-U of the image plane of the ultrasound transducer 26. Longitudinal movement of the transducer cradle 52 may be accomplished by sliding the transducer cradle 52 longitudinally on a support rod 56. The support rod 56 is rigidly mounted to the transducer mount base 54 by a mounting bracket 58. The transducer cradle 52 is slidably supported on the support rod 56 by a support bracket 59 secured to the transducer cradle 52. A knob 57 at an end of the support rod 56 prevents the transducer cradle 52 from sliding off the support rod 56 and also acts as a brake when the knob 57 is turned about the longitudinal axis of the support rod 56. Adjusting the longitudinal position of the transducer cradle 52 on the support rod 56 adjusts the longitudinal position of the ultrasound transducer 26 supported thereon.

FIG. 11A, FIG. 11B and FIG. 11C illustrate the needle gun mount 40 and the ultrasound transducer mount 50 in three different relative arcuate positions, with FIG. 11A showing the mounts 40, 50 as far apart as possible on the mounting plate 31, and FIG. 11B showing the mounts 40, 50 as close as possible on the mounting plate 31. In all three illustrations, the longitudinal position of the biopsy needle 27 remains unchanged in an extended configuration beyond the RCM. It is evident comparing FIG. 11A, FIG. 11B and FIG. 11C that the position of the RCM does not change irrespective of the relative arcuate locations of the mounts 40, 50. This is true whether the mounting plate 31 is arcuately moved on the mount structure 29, whether the ultrasound transducer mount 50 is arcuately moved on the mounting plate 31, or whether both are moved. Thus, the longitudinal axis N-N of the needle gun 25, which defines the path along which the biopsy needle 27 follows during the breast biopsy, intersects the longitudinal centerline U-U of the image plane of the ultrasound transducer 26 at the RCM. The longitudinal axis N-N, the centerline U-U and the RCM are all in the common plane, and rotation of the biopsy guide 30 about the RCM does not change that the longitudinal axis N-N and the centerline U-U intersect at the RCM. In this manner the needle gun 25 and the ultrasound transducer 26 can be positioned arcuately in the most convenient positions on the biopsy guide 30 without affecting the accuracy of the biopsy operation.

Figure 12C:
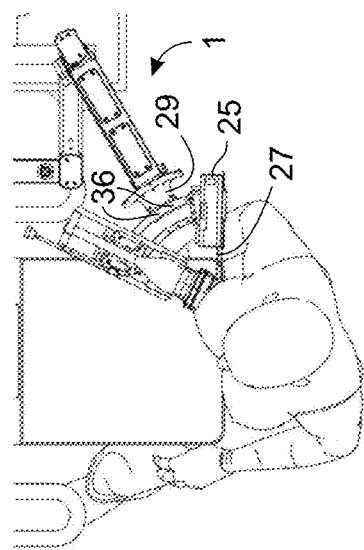
FIG. 12C depicts the FIG. 12B with the needle gun further longitudinally advanced so that the biopsy needle has penetrated into the breast.
Figure 12B:
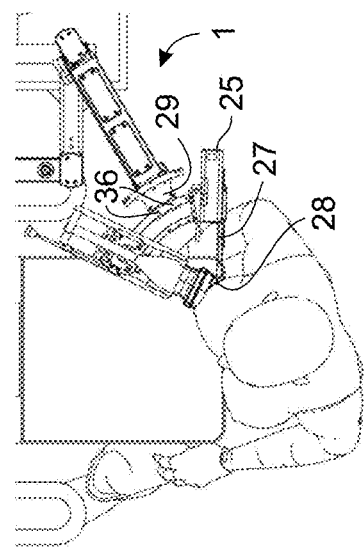
FIG. 12B depicts FIG. 12A with the needle gun longitudinally advanced to place a tip of a biopsy needle on the needle gun directly adjacent the breast of the subject.
Figure 12A:
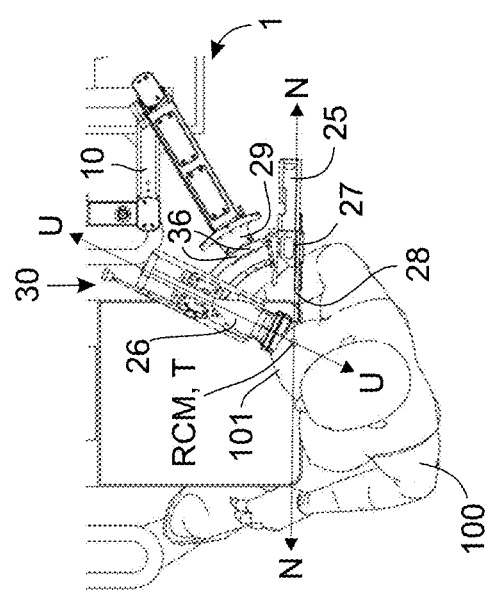
FIG. 12A depicts a top view of the apparatus of FIG. 1 having a needle gun and an ultrasound transducer mounted thereon with the needle gun in a longitudinal position most distant from a breast of a subject.
Figure 15:
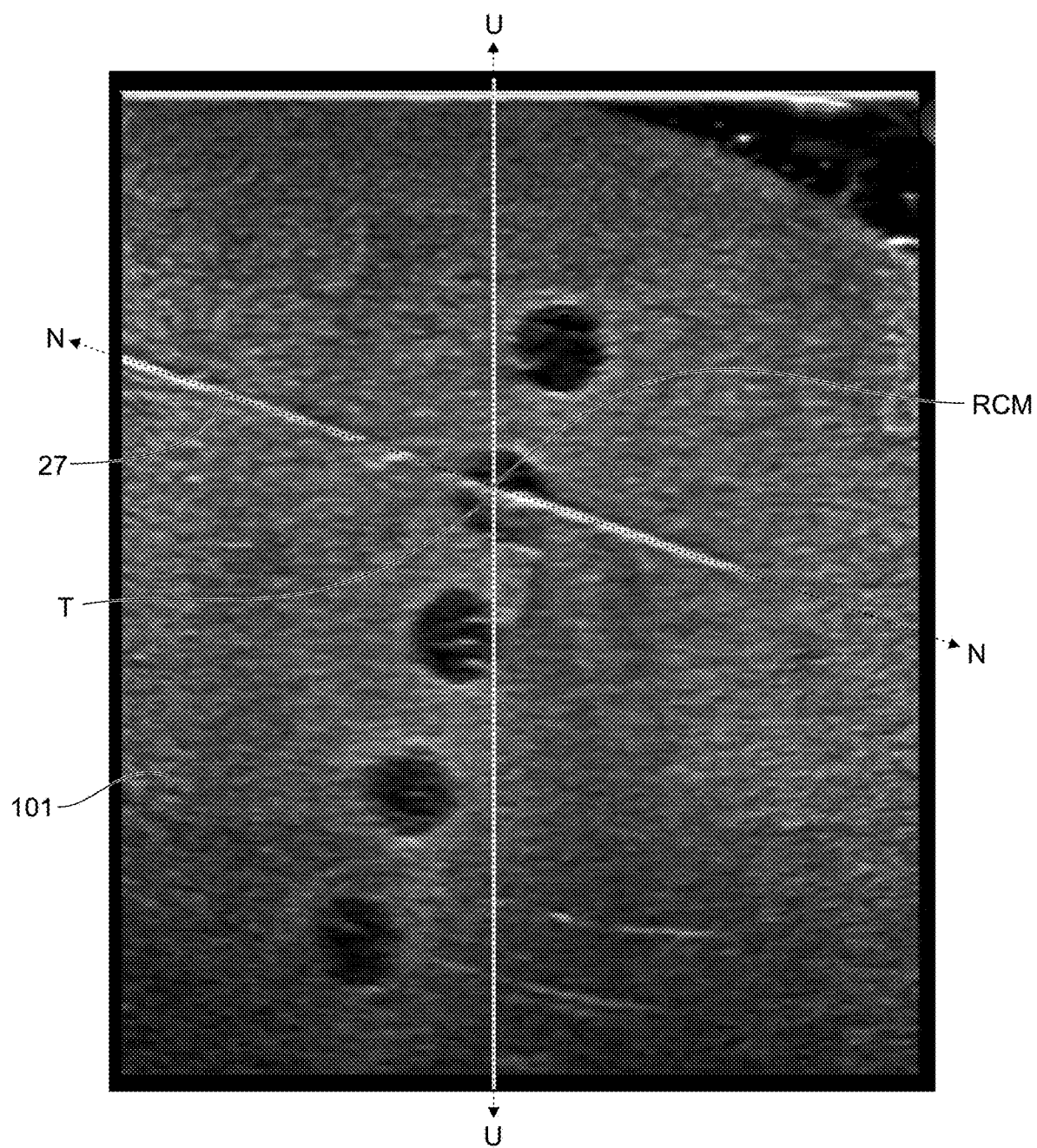
FIG. 15 depicts an ultrasound live image of the biopsy needle sampling the target tumor in the breast.

FIG. 12A, FIG. 12B and FIG. 12C illustrate the apparatus 1 in association with the parallel plate radiology imager 70, the apparatus 1 in position to perform the breast biopsy. Thus, the RCM of the biopsy guide 30 has been aligned with the target tumor T in the breast 101 of the subject 100. FIG. 12A shows the needle gun 25 in a longitudinal position most distant from the breast 101, in which a tip 28 of the biopsy needle 27 is distant from the breast 101. In performing the breast biopsy, the surgeon or surgical robot pushes the needle gun 25 to advance the needle 25 gun along the longitudinal axis N-N. FIG. 12B depicts the needle gun 25 longitudinally advanced to place the tip 28 of the biopsy needle 27 directly adjacent the breast 101. Continued pushing of the needle gun 25 further advances the tip 28, which penetrates the breast 101 until the biopsy needle 27 is sufficiently deep into the breast 101 that the biopsy needle 27 intersects the target tumor T, at which time the biopsy needle 27 may be manipulated to extract a sample of the tumor. The position of the needle gun 25 at this stage of the biopsy procedure is shown in FIG. 12C. The biopsy needle 27 is then extracted from the breast 101 by pulling the needle gun 25 back along longitudinal axis N-N. The entire procedure of needle penetration and extraction is simply, smoothly and arcuately accomplished because the biopsy guide 30, with the needle gun 25 and ultrasound transducer 26 supported thereon, is stably mounted on the support system 10 and arcuately positioned relative to a fixed point in space (i.e. the target tumor T) as determined from a radiology image. No or minimal error arising from surgeon manipulation is introduced into the biopsy procedure, and any deviations from the correct path, established from the radiology image, of the biopsy needle 27, which might arise during the procedure can be instantly noted through real time ultrasound imaging so that the surgeon or surgical robot can take corrective measures. A live ultrasound image of the biopsy needle 27 sampling the target tumor T in the breast 101 is shown in FIG. 15.

FIG. 13A to FIG. 13J illustrate a method of performing a breast biopsy with the aid of the apparatus 1 in association with position emission mammography (PEM) imaging. FIG. 14A and FIG. 14B show PEM images illustrating alignment of the RCM of the biopsy guide 30 with the target tumor T during the method.

Figure 13B:
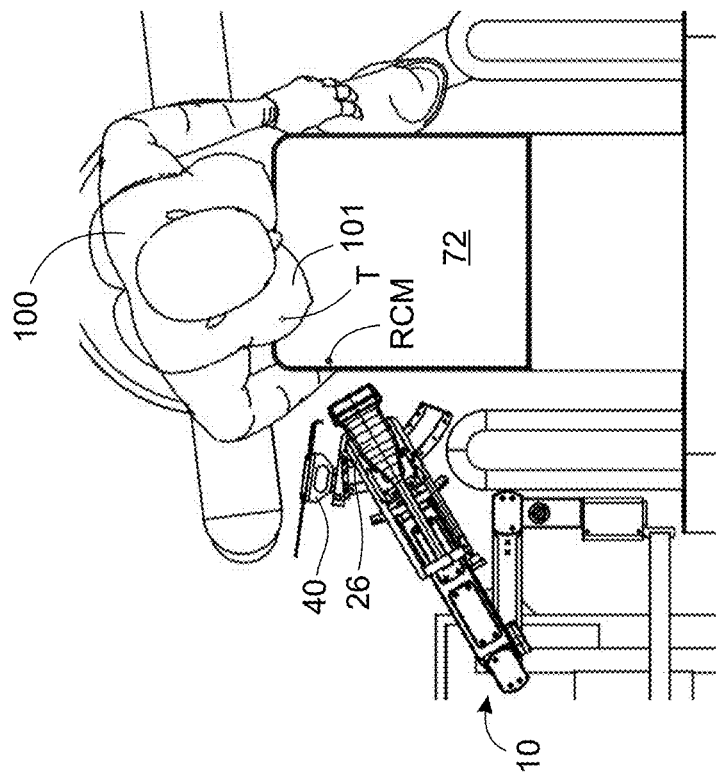
FIG. 13A, FIG. 13B, FIG. 13C, FIG. 13D, FIG. 13E, FIG. 13F, FIG. 13G, FIG. 13H, FIG. 13I and FIG. 13J depict a series of operations of the apparatus of FIG. 1 showing how the apparatus may be used for assisting breast biopsy in association with parallel plate radiology imaging.
Figure 13A:
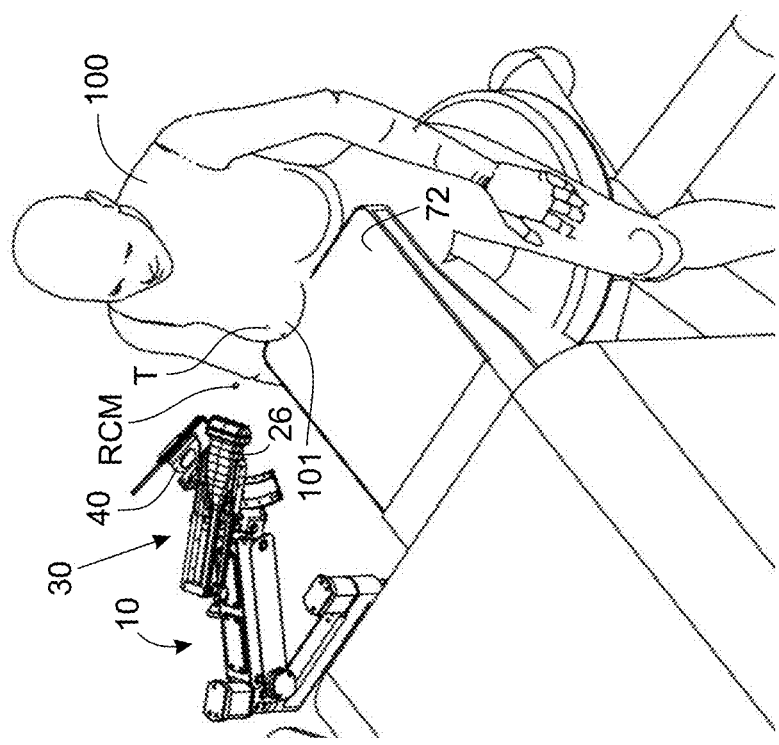
Figure 14B:
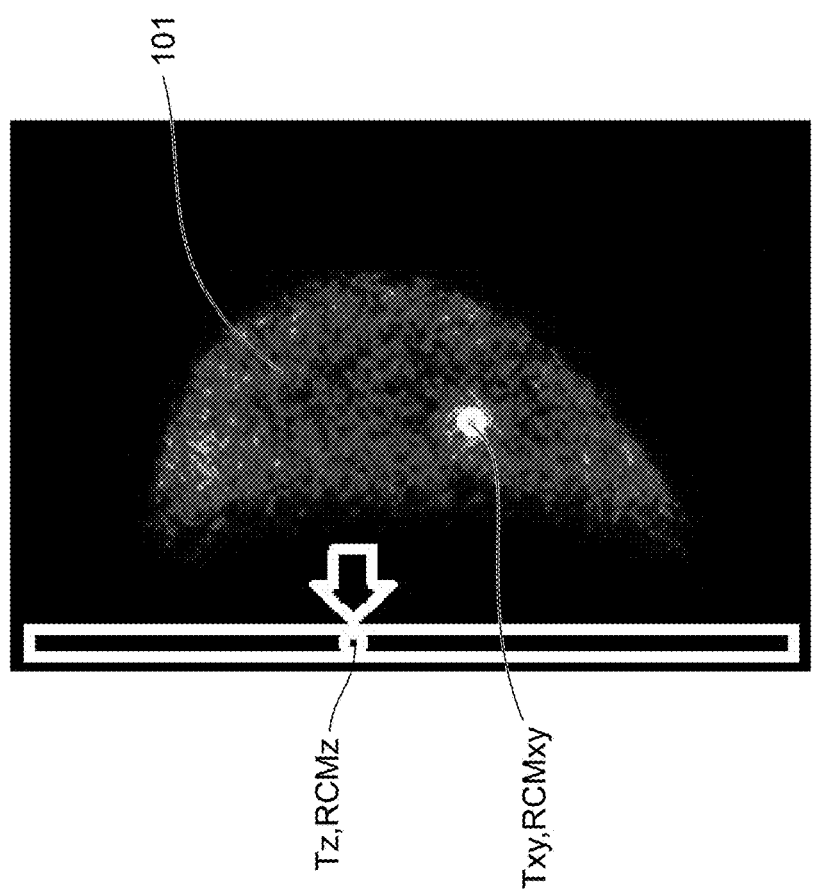
FIG. 14A and FIG. 14B depict a series of positron emission mammography (PEM) images illustrating that registration of a coordinate system of the apparatus shown in FIG. 13A with a coordinate system on the PEM images can be used to determine whether a remote center of motion (RCM) of a biopsy guide of the apparatus is aligned on a hotspot in the PEM image, the hotspot identifying location of a target tumor in the breast.
Figure 14A:
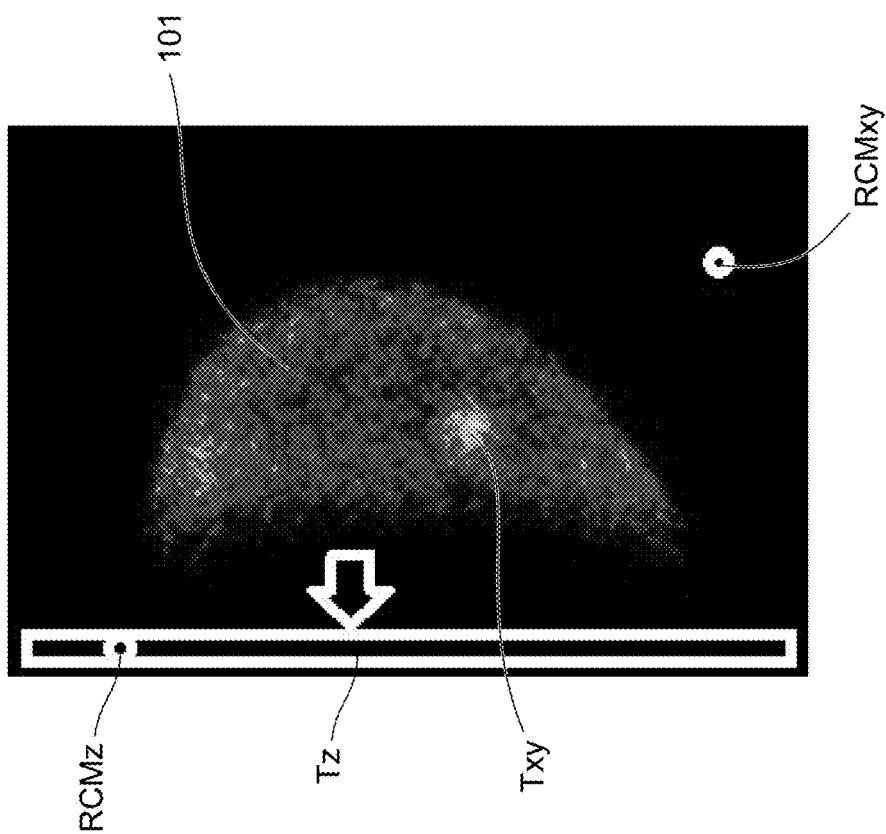

FIG. 13A and FIG. 13B show the subject 100 seated at the parallel plate radiology imager 70, in this case a PEM imager, with her breast 101, having the target tumor T therein, placed on the upper surface of the lower plate 72 of the imager 70. The upper plate of the imager 70 is omitted for clarity, but in practice, the upper plate would be above, and applying light pressure to, the breast 101. The apparatus 1 for assisting the breast biopsy is positioned at the same side of the subject 100 as the breast 101 being biopsied. The biopsy guide 30 supported on the support system 10 of the apparatus 1 is randomly positioned and the remote center of motion RCM of the biopsy guide 30 is somewhere in space, not between the parallel plates of the imager 70. The ultrasound transducer 26 is mounted on the biopsy guide 30, but no needle gun is yet present on the biopsy guide 30. At this stage, 3D positional data of the biopsy guide 30 is collected by the position encoders 4, 5, 6 of the apparatus 1 and transmitted to the computer 3, which performs the necessary calculations to provide a 3D position of the RCM in space. Further, a 3D PEM image of the breast 101 is obtained and a radioactive hotspot on the image locates the 3D position of the tumor T in the breast 101, which is shown in the PEM image in FIG. 14A. Using the computer 3, the 3D position of the RCM is then registered on a coordinate system in the PEM image to provide an overlay of the position of the RCM on the PEM image, which can be shown on the monitor 23 for the operator to consult. The PEM image in FIG. 14A shows the registered position of the RCM in the coordinate system of the image, where a z-position RCMz and an x-y position RCMxy of the RCM of the biopsy guide 30 are not aligned with a z-position Tz and an x-y position Txy of the target tumor T in the breast 101.

Figure 13D:
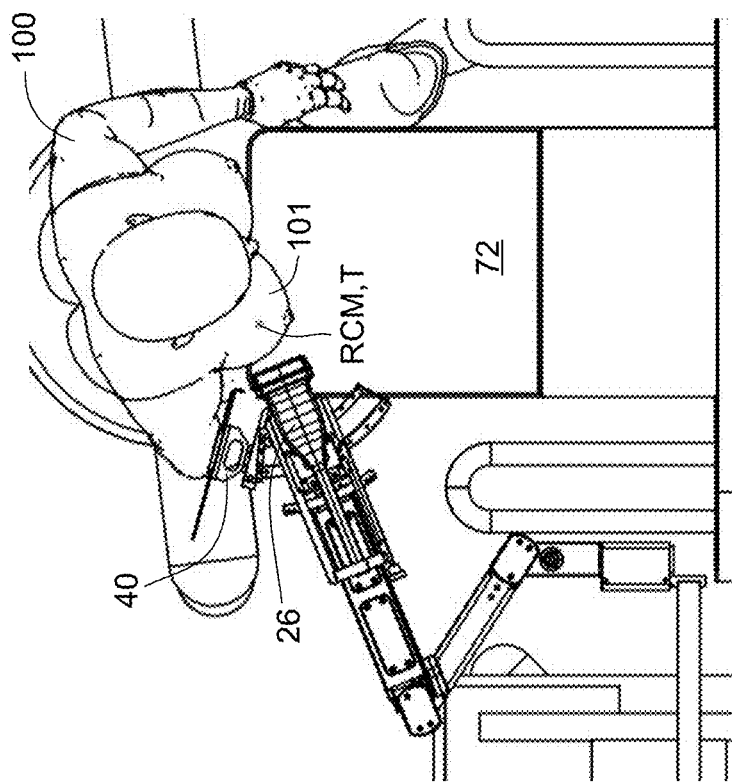
Figure 13C:
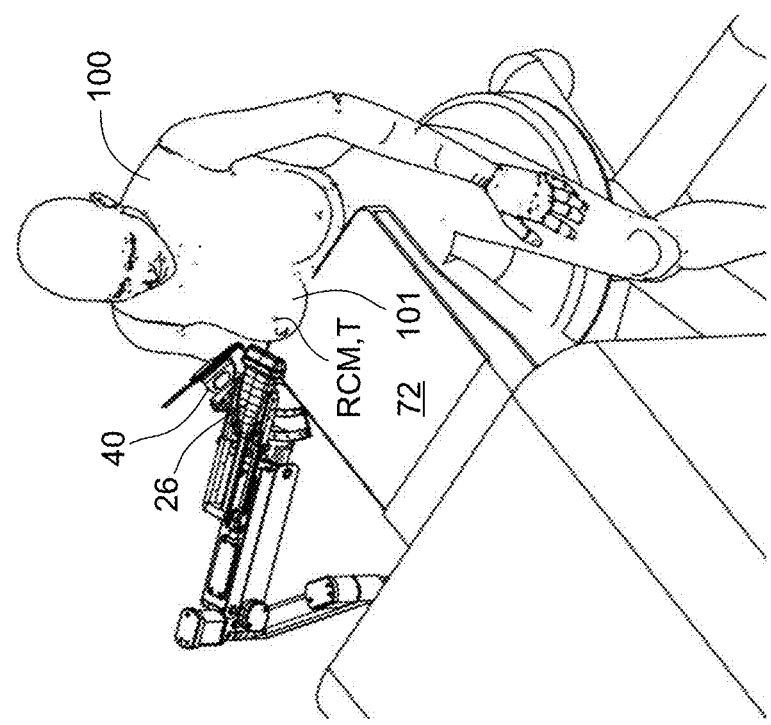

Based on the 3D position of the RCM relative to the 3D position of the target tumor T as viewed in the PEM image, the operator then manipulates the arms 9 and 11 and the parallelogram (comprising arms 12, 13) of the support system 10 to progressively move the RCM toward the target tumor T in an effort to align the coordinates of the RCM with the coordinates of the target tumor T on the PEM image. The computer 3 can calculate the results of each movement, showing the results on the PEM image in real time. Provided the subject 100 does not move, the single PEM image acquired is sufficient to undertake alignment of the RCM with the target tumor T. However, it may be necessary or desirable to acquire another PEM image once alignment has been completed to confirm that the positions of the RCM and the target tumor T are aligned. FIG. 13C and FIG. 13D show the configuration of the apparatus 1 with the biopsy guide 30 mounted thereon in relation to the subject 100 once the RCM and the target tumor T are aligned. FIG. 14B illustrates the PEM image when the RCM and the target tumor T are aligned.

Figure 13F:
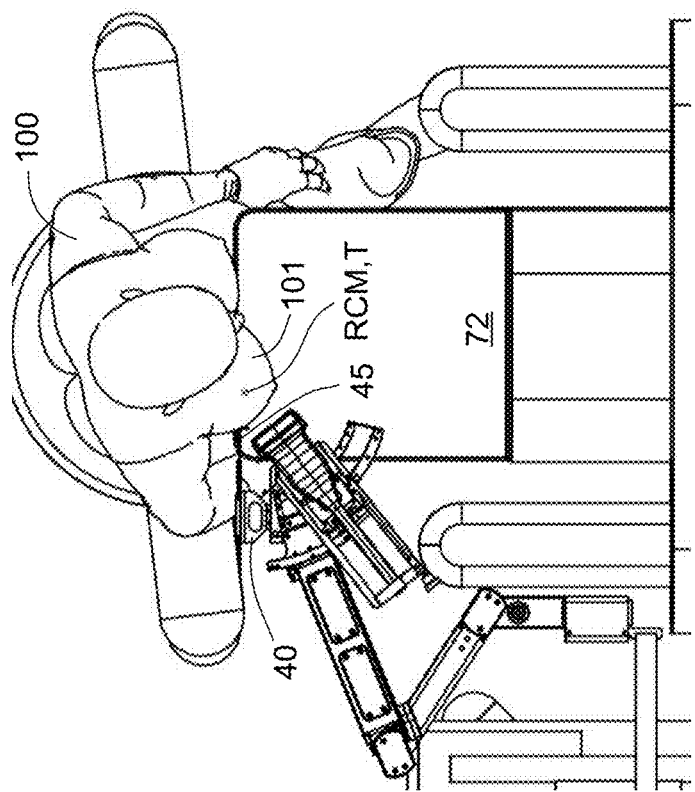
Figure 13E:
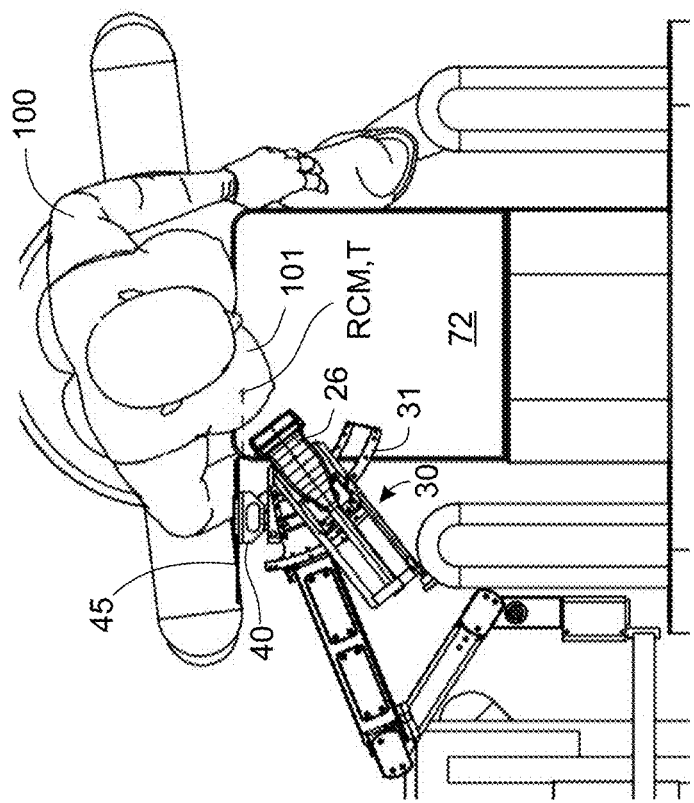
Figure 13H:
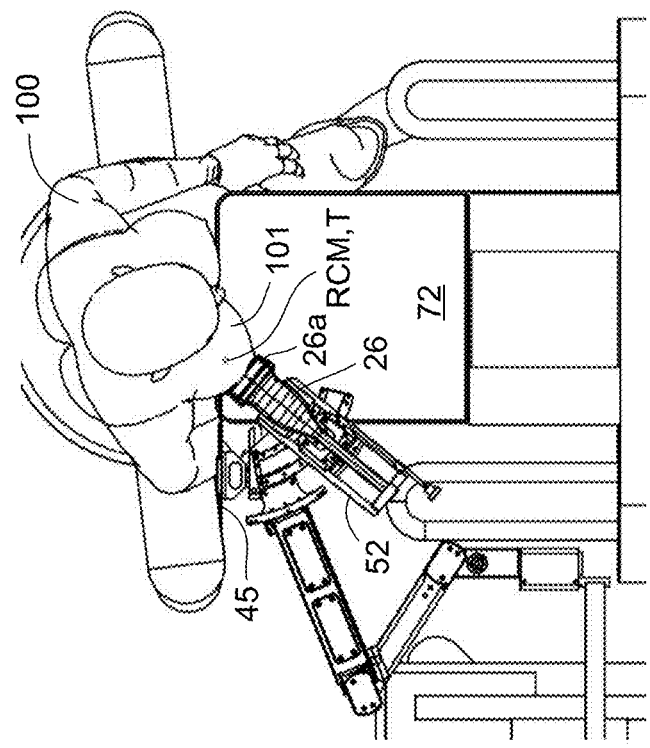
Figure 13G:
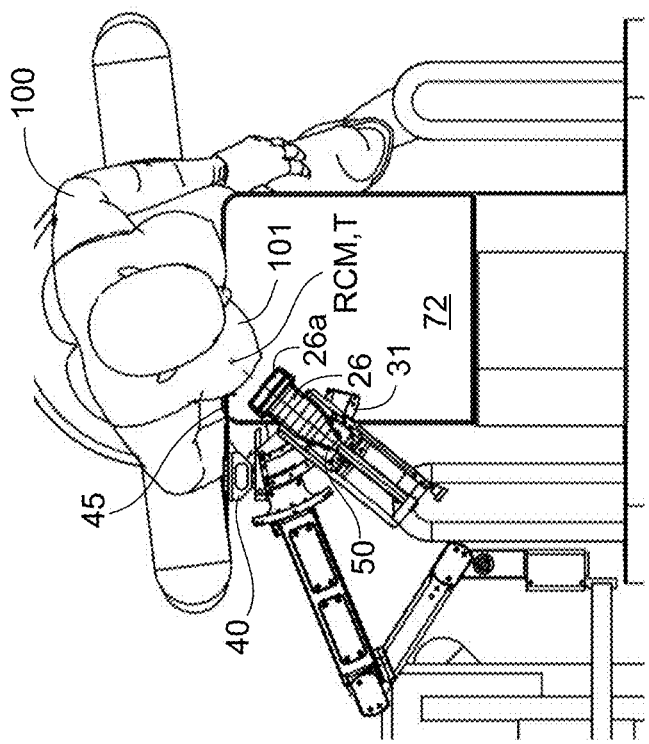

In the next steps, other preliminary manipulations of the biopsy guide 30 are done to set up the apparatus 1. As seen in FIG. 13E in comparison to FIG. 13D, the mounting plate 31 of the biopsy guide 30 can be moved arcuately on the mount structure 29 to a position where a needle gun when mounted on the needle gun mount 40 will have a longitudinal axis substantially parallel to a chest wall of the subject 100 so that the biopsy needle can penetrate the breast 101 from the side, which is how a breast biopsy is normally performed. As seen in FIG. 13F in comparison to FIG. 13E, the needle support 45 may then be moved longitudinally up to the skin of the subject's breast 101 in preparation for when a needle gun will be mounted on the needle gun mount 40. As seen in FIG. 13G in comparison to FIG. 13F, the transducer mount 50 may then be moved arcuately on the mounting plate 31 of the biopsy guide 30 to a position where the ultrasound transducer 26 does not interfere with the needle support 45 and which would maximize contact area of a head 26a of the ultrasound transducer 26 with the skin of the subject's breast 101 when the head 26a is brought into contact with the breast 101. As seen in FIG. 13H in comparison to FIG. 13G, the transducer cradle 52 may then be advanced longitudinally to bring the head 26a of the ultrasound transducer 26 into contact the skin of the subject's breast 101 at the position where the maximum contact area can be realized.

Figure 13J:
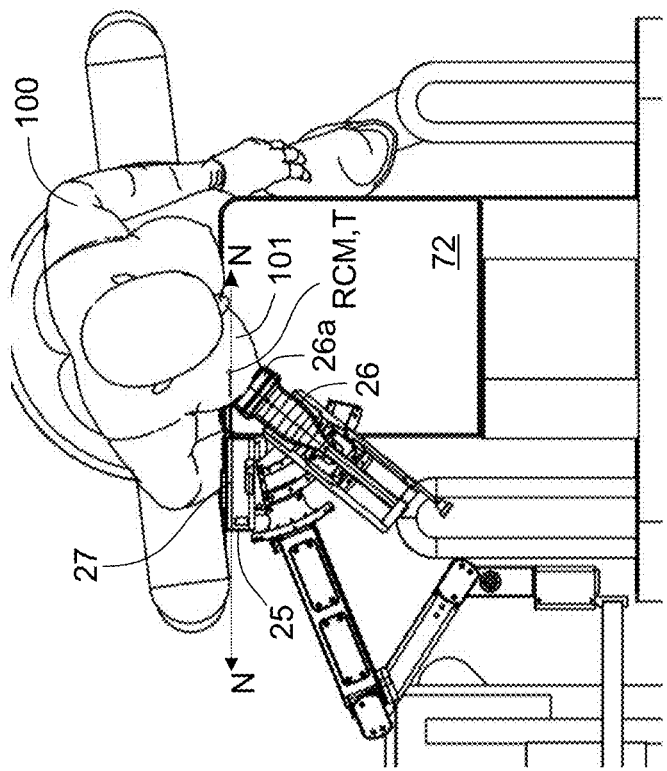
Figure 13I:
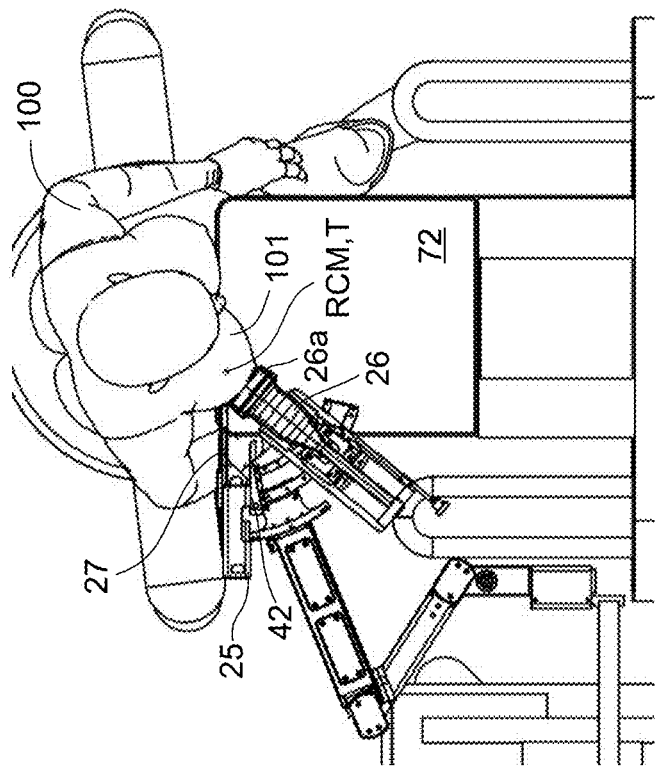

At this stage, the needle gun 25 may be mounted on the needle gun cradle 42 of the needle gun mount 40, as seen in FIG. 13I. With the needle gun 25 mounted on the needle gun cradle 42, the needle gun 25 may be advanced longitudinally on the needle gun cradle 42 to insert the biopsy needle 27 into the breast 101 to the target tumor T, as seen in FIG. 13J. The needle support 45 helps keep the biopsy needle 27 on the correct path to the target tumor T, and real time ultrasound images from the ultrasound transducer 26 help verify that the biopsy needle 27 remains on the correct path. After the biopsy needle 27 takes a sample of the target tumor T, the biopsy needle 27 is extracted by reversing the longitudinal movement of the needle gun 25.

It is a particular advantage that other preliminary manipulations of the biopsy guide 30 may be done after the alignment of the RCM with the target tumor T, but before a needle gun is mounted on the biopsy guide 30. Once the biopsy guide 30 has reached its final position based on the alignment of the RCM with the target tumor T, any arcuate movements of the biopsy guide 30, any arcuate movements of the ultrasound transducer mount 50 on the biopsy guide 30 and any longitudinal movements of the needle gun 25 and the ultrasound transducer mount 50 on the biopsy guide 30 will not affect the position of the RCM, so realignment of the RCM with the target tumor T would not be necessary. This permits mounting of the needle gun 25 itself on the biopsy guide 30 to be one of the last steps performed before inserting the biopsy needle 27 into the breast 101.

Figure 16B:
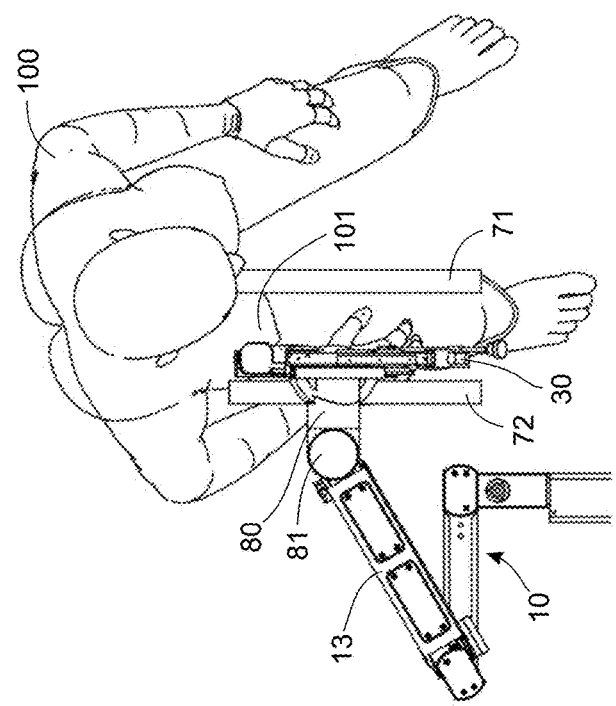
FIG. 16B depicts a top view of the apparatus of FIG. 16A.
Figure 16A:
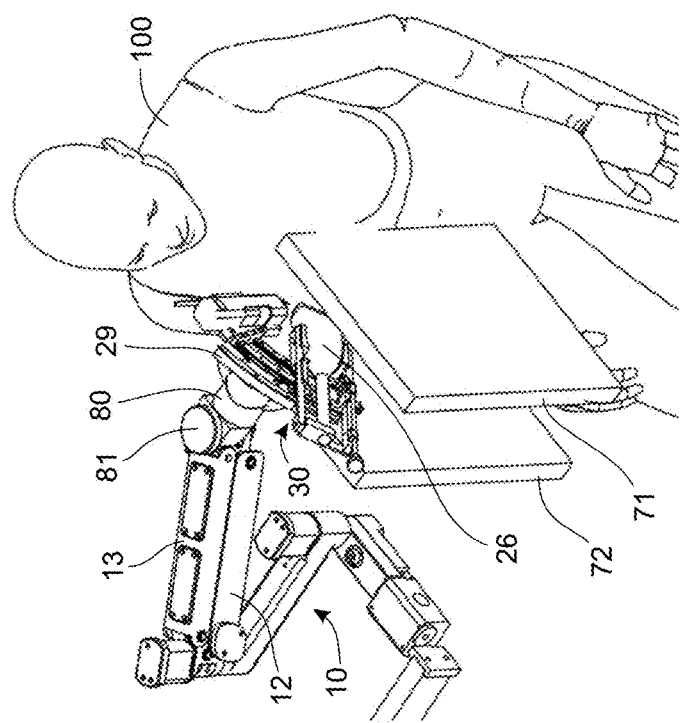
FIG. 16A depicts a perspective view of the apparatus for assisting breast biopsy adapted for mediolateral breast imaging and biopsy where the parallel plates of the radiology imager are vertically oriented instead of horizontally oriented.

FIG. 1 to FIG. 10 depict the apparatus 1 in an orientation where the biopsy guide 30 is horizontally oriented and therefore adapted for a craniocaudal mode of breast imaging and biopsy where the parallel plates 71, 72 of the parallel plate radiology imager 70 are oriented horizontally with respect to the ground. In mediolateral breast imaging and biopsy, the parallel plates 71, 72 of the parallel plate radiology imager 70 are vertically oriented with respect to the ground instead of horizontally oriented as seen in FIG. 16A and FIG. 16B. In order to adapt the apparatus 1 for mediolateral breast imaging and biopsy, an adjustable adapter assembly 80 may be used to connect the mount structure 29 to the support system 10 so that the biopsy guide 30 is vertically oriented, as shown in FIG. 16A and FIG. 16B. In the embodiment illustrated in FIG. 16A to FIG. 18C, the adjustable adapter assembly 80 is securely connected by set screws to the mount structure 29, and securely connected by a threaded knob 81 to the support system 10 at distal ends of the third and fourth arms 12, 13.

As seen in FIG. 17A, FIG. 17B and FIG. 17C, the adjustable adapter assembly 80 comprises four machined components: a horizontal-to-vertical adapter body 82; a roll adjustment block 83; a yaw adjustment link 84; and, a curved washer 85. The four machine components 82, 83, 84 and 85 are assembled together by a shoulder bolt 86 inserted through a washer 87 and an arcuate slot in the yaw adjustment link 84 to be threaded into a threaded boss 88 fixedly attached to and extending outwardly from an inner face 89 of the horizontal-to-vertical adapter body 82. The threaded boss 88 extends into a through-aperture 90 in the roll adjustment block 83 so that the roll adjustment block 83 can pivot freely on the threaded boss 88. Once the four components 82, 83, 84 and 85 are assembled, the adjustable adapter assembly 80 becomes rigid except for the yaw adjustment link 84, which freely pivots between the curved washer 85 and the roll adjustment block 83 about the RCM of the biopsy guide 30 (see FIG. 18A, FIG. 18B and FIG. 18C).

The horizontal-to-vertical adapter body 82 comprises the inner face 89, which interfaces with a first face of the roll adjustment block 83. The horizontal-to-vertical adapter body 82 also comprises an outer face 91 that is oriented substantially orthogonally in respect of the inner face 89 and shares and edge with the inner face 89 The outer face 91 is mounted to the support system 10 at distal ends of the third and fourth arms 12, 13 at same location where the mount structure 29 is mounted to the support system 10 when the adjustable adapter assembly 80 is not used. The outer face 91 comprise a large aperture 92 through which the threaded knob 81 is inserted to secure the horizontal-to-vertical adapter body 82 to the support system 10. Horizontal orientation of the horizontal-to-vertical adapter body 82 is fixed by the location of a pin 93 relative to one or more mating holes (not shown) in support system 10. The orthogonal relationship between the outer face 91 and the inner face 89 of the horizontal-to-vertical adapter body 82 gives rise vertically orienting the biopsy guide 30.

The roll adjustment block 83 has a body, in which the first face is at one end and a second face 96 is at the opposed end of the body. The through-aperture 90 extends longitudinally through the body of the roll adjustment block 83 between the first and second faces. The second face 96 comprises an arcuate channel 97 therein having a channel axis across a diameter of the second face 96. The roll adjustment block 83 can pivot freely on the threaded boss 88 in the absence of a restraint. However, the rotational orientation of the roll adjustment block 83 about a longitudinal axis through the threaded boss 88 can be fixed by restraining rotation of the roll adjustment block 83 with a mating pin 94 inserted into one of a plurality of index holes 95 (only one labeled) arranged in a circular configuration in the inner face 89 of the horizontal-to-vertical adapter body 82 and into one of a plurality of holes (not shown) arranged in a circular configuration in the first face of the of the roll adjustment block 83. With the mating pin 94 inserted into a hole in the inner face 89 of the horizontal-to-vertical adapter body 82 and a hole in the first face of the roll adjustment block 83, the roll adjustment block 83 is restrained in a fixed rotational position relative to the horizontal-to-vertical adapter body. FIG. 17B and FIG. 17C illustrate two different rotational positions for the roll adjustment block 83 having an angular separation of 30° about the longitudinal axis through the threaded boss 88. The position shown in FIG. 17B is called a neutral position, which fixes the RCM at a point located directly below the roll adjustment block 83, while the position shown in FIG. 17C will move the RCM toward the subject 100. Moving the RCM toward the subject 100 provides more space for the biopsy guide 30 between the support system 10 and the subject 100. The position shown in FIG. 17C is useful for performing a biopsy on targets in the breast 101 close to the chest wall of the subject 100. Thus, the adjustable adapter assembly 80 can be assembled in various fixed configurations to accommodate targets in difficult to reach locations, such as near the chest wall of the subject 100.

Figure 18A:
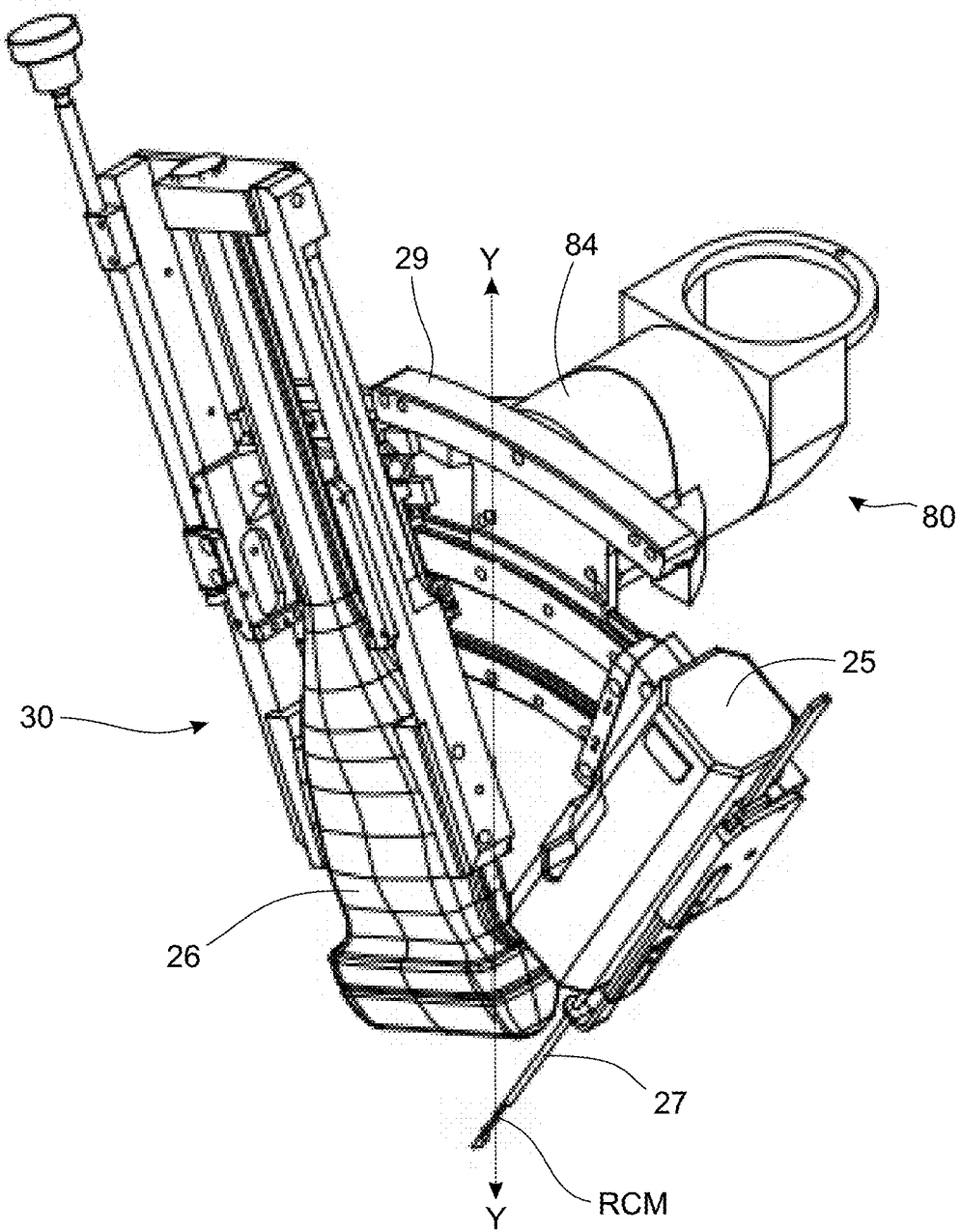
FIG. 18A depicts a perspective view of a biopsy guide of the apparatus of FIG. 16A attached to the adjustable adapter assembly of FIG. 17B.
Figure 18B:
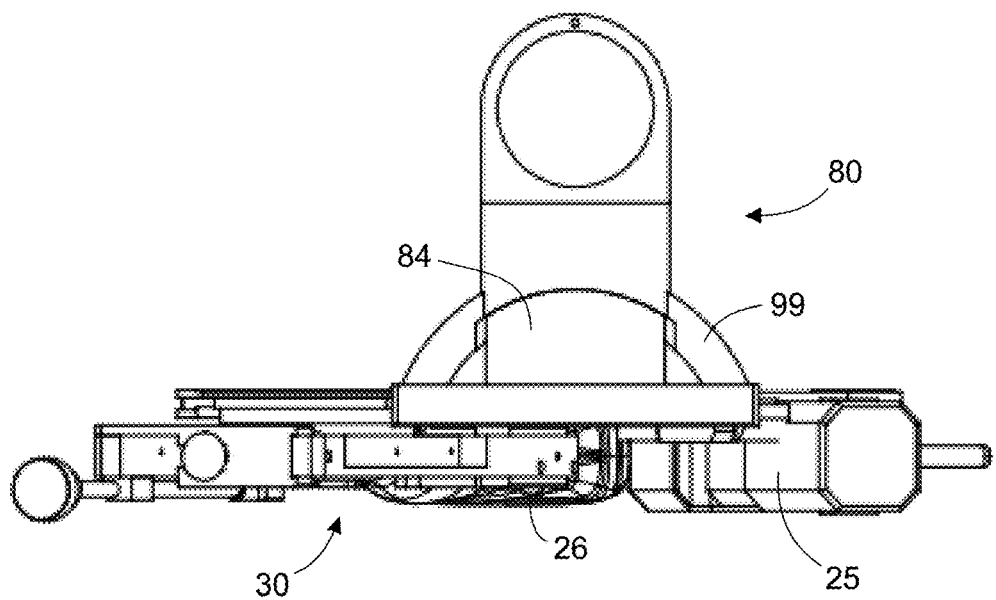
FIG. 18B and FIG. 18C depict top views of FIG. 18A showing extent of yaw adjustment permitted when the biopsy guide is attached to the adjustable adapter assembly.
Figure 18C:
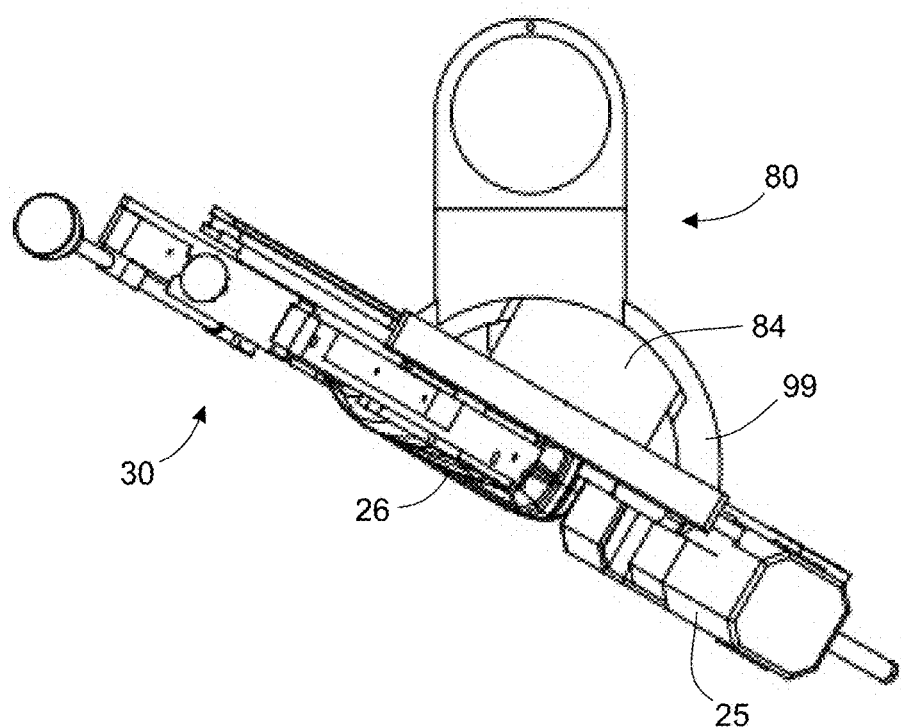

The yaw adjustment link 84 comprises a body having a rear face that interfaces with the second face 96 of the roll adjustment block 83, and a front face 98 that interfaces with and is mounted to the mount structure 29, the biopsy guide 30 being mounted on the mount structure 30. The front face 98 of the yaw adjustment link 84 is provided with screw holes 79 (only one labeled) that mate with corresponding screw holes in the mount structure 29 so that the adjustable adapter assembly 80 can be mounted to the mount structure 29 using set screws. The yaw adjustment link 84 further comprises an arcuate rocker beam 99 having a convex rear face and a concave front face. The arcuate rocker beam 99 is complementary to and mates with the arcuate channel 97 in the second face 96 of the roll adjustment block 83. The arcuate rocker beam 99 comprises the arcuate slot (not shown) therein through which the shoulder bolt 86 is inserted. The yaw adjustment link 84 is pivotally connected to the roll adjustment block 83 so that pivoting of the yaw adjustment link 84 about an axis orthogonal to the longitudinal axis through the threaded boss 88 and orthogonal to the channel axis permits freely adjusting a yaw angle of the biopsy guide 30. Pivoting of the yaw adjustment link 84 is permitted because the arcuate slot has sufficient tolerance on each side of the shoulder bolt 86 to permit the front face of arcuate rocker beam 99 to move along the arc of the arcuate channel 97 and the rear face of arcuate rocker beam 99 to move along the curve of the curved washer 85 when the adjustable adapter assembly 80 is assembled with the shoulder bolt 86 in place. Referring to FIG. 18A, FIG. 18B and FIG. 18C, the adjustable adapter assembly 80 is illustrated attached to the mount structure 29 with the biopsy guide 30 mounted on the mount structure 29. With the adjustable adapter assembly 80 oriented horizontally, the biopsy guide 30 is oriented vertically. A yaw axis Y-Y about which the yaw adjustment link 84 pivots intersects the RCM of the biopsy guide 30 when the biopsy guide 30 is attached to the adjustable adapter assembly 80 through the mount structure 29, and the biopsy guide 30 is moved to change the yaw angle of the yaw axis Y-Y so that the biopsy guide 30 can fit between the parallel plates 71 and 72. Since the position of the RCM relative to the biopsy guide 30 does not move when the yaw angle of the yaw axis Y-Y is changed, adjustment of the yaw angle can be made to align the biopsy guide 30 to fit between the parallel plates after the RCM is aligned with the target in the PEM image. Adjustment of the yaw angle is particularly useful for performing a biopsy on a target located near a plate 71 or 72 of the parallel plate radiology imager 70. FIG. 18B and FIG. 18C show that the extent of yaw angle adjustment from a neutral position (FIG. 18B) can be up to ±30°, where FIG. 18C shows a yaw adjustment of +30°.

The novel features will become apparent to those of skill in the art upon examination of the description. It should be understood, however, that the scope of the claims should not be limited by the embodiments, but should be given the broadest interpretation consistent with the wording of the claims and the specification as a whole.

The invention claimed is:

1. An apparatus for assisting breast biopsy in association with parallel plate radiology imaging, the apparatus comprising:
   a biopsy guide comprising
      a mounting plate comprising one or more arcuate tracks,
      a needle gun mount mounted on the mounting plate, the needle gun mount of the mounting plate slidably supported on the one or more arcuate tracks, and
      an ultrasound transducer mount mounted on the mounting plate, the ultrasound transducer mount slidably supported on the one or more arcuate tracks, the ultrasound transducer mount mounted on the mounting plate in a common plane as the needle gun mount,
      wherein a biopsy needle of a needle gun when mounted on the needle gun mount and an image plane of an ultrasound transducer when mounted on the ultrasound transducer mount have longitudinal axes in or parallel to the common plane, the longitudinal axes intersecting at a remote center of motion (RCM) remote from the biopsy guide,
      wherein the needle gun mount is configured to slidably support the needle gun for longitudinal movability parallel to the longitudinal axis of the biopsy needle and wherein the ultrasound mount is configured to slidably support the ultrasound transducer for longitudinal movability parallel to the longitudinal axis of the image plane,
      wherein the needle gun when mounted on the needle gun mount and the ultrasound transducer when mounted on the ultrasound transducer mount are independently moveable parallel to the respective longitudinal axes of the biopsy needle and image plane, whereby a position of the RCM with respect to the biopsy guide is unchanged when the needle gun and/or ultrasound transducer is moved parallel to the respective longitudinal axes,
      and wherein the needle gun when mounted on the needle gun mount and the ultrasound transducer when mounted on the ultrasound transducer mount are independently arcuately moveable about the RCM along a common arcuate path, whereby the longitudinal axes move arcuately about the RCM when the needle gun and ultrasound transducer move along the common arcuate path, wherein a position of the RCM with respect to the biopsy guide is unchanged when the needle gun and/or the ultrasound transducer is moved along the common arcuate path on the mounting plate.

2. The apparatus of claim 1, further comprising the needle gun mounted on the needle gun mount and the ultrasound transducer mounted on the ultrasound transducer mount.

3. The apparatus of claim 1, wherein the arcuate track comprises two spaced-apart parallel arcuate tracks in the common plane.

4. The apparatus of claim 1, wherein the needle gun mount comprises a needle gun cradle on which the needle gun is mounted and a needle gun base to which the needle gun cradle is rigidly attached, the needle gun moveable in the needle gun cradle along the longitudinal axis of the needle.

5. The apparatus of claim 4, wherein the needle gun mount further comprises a needle gun stop and wherein longitudinal movability of the needle gun parallel to the longitudinal axis of the biopsy needle is lockable or stoppable to prevent the longitudinal movability by way of the needle gun stop.

6. The apparatus of claim 1, wherein the ultrasound transducer mount comprises a transducer cradle on which the ultrasound transducer is mounted and a transducer cradle base on which the transducer cradle is movably mounted, the transducer cradle moveable on the transducer cradle base along the longitudinal axis of the image plane of the ultrasound transducer.

7. The apparatus of claim 1, wherein the needle gun mount comprises an extendible needle support that reduces lateral deflection of the biopsy needle when the biopsy needle enters the breast of the subject.

8. The apparatus of claim 1, wherein the apparatus further comprises structures for effecting three-dimensional movement of the biopsy guide comprising a plurality of support arms pivotably connected to each other, at least one of the support arms connected to a stationary base and at least one of the support arms connected to the biopsy guide.

9. The apparatus of claim 1, wherein the apparatus further comprises a system for registering coordinates of the RCM with a coordinate system on an image of a breast of a subject obtained from a parallel plate radiology imager, the system for registering coordinates comprising one or more position encoders for locating the RCM in space and a computer programmed with computer executable instructions for comparing the location of the RCM to position-related image data collected from the parallel plate radiology imager, the one or more position encoders in electronic communication with the computer.

10. The apparatus of claim 1, wherein the parallel plate radiology imager performs X-ray mammography, stereo X-ray mammography, tomosynthesis or positron emission mammography (PEM).

* * * * *